United States Patent
Daley et al.

(10) Patent No.: US 6,733,746 B2
(45) Date of Patent: *May 11, 2004

(54) HEMATOPOIETIC CELL CULTURE NUTRIENT SUPPLEMENT

(75) Inventors: John P. Daley, Buffalo, NY (US); Barbara M. Dadey, East Aurora, NY (US); William C. Biddle, Buffalo, NY (US); Michelle G. Wysocki, Cheektowaga, NY (US)

(73) Assignee: Invitrogen Corporation, Carlsbad, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 47 days.

(21) Appl. No.: 08/792,299

(22) Filed: Jan. 31, 1997

(65) Prior Publication Data

US 2001/0033835 A1 Oct. 25, 2001

Related U.S. Application Data

(60) Provisional application No. 60/013,149, filed on Mar. 12, 1996.

(51) Int. Cl.$^7$ .......... A01N 63/00; A01N 65/00; A61K 48/00; C12N 5/00
(52) U.S. Cl. .......... 424/93.21; 424/93.1; 424/93.2; 435/372; 435/383; 435/384; 435/386; 435/387; 435/388; 435/389; 435/404; 435/405; 435/406; 435/407
(58) Field of Search .......... 424/93.21; 435/240.2, 435/320.1, 244, 384, 385, 386, 378, 948, 388, 389, 404, 405, 407; 536/24.1, 23.1

(56) References Cited

U.S. PATENT DOCUMENTS

| | | | |
|---|---|---|---|
| 4,673,649 A | 6/1987 | Boyce et al. | 435/378 |
| 4,767,704 A | 8/1988 | Cleveland et al. | 435/70.2 |
| 4,927,762 A | * 5/1990 | Darfler | 435/387 |
| 5,024,947 A | 6/1991 | Inlow et al. | 435/404 |
| 5,045,454 A | 9/1991 | Bertheussen | 435/29 |
| 5,061,620 A | 10/1991 | Tsukamoto et al. | 435/7.21 |
| 5,063,157 A | 11/1991 | Stockinger | 435/387 |
| 5,122,469 A | 6/1992 | Mather et al. | 435/383 |
| 5,128,259 A | * 7/1992 | Morgan | 435/372 |
| 5,316,938 A | 5/1994 | Keen et al. | 435/404 |
| 5,336,614 A | 8/1994 | Brown et al. | 435/397 |
| 5,342,777 A | * 8/1994 | Cole et al. | 435/378 |
| 5,359,046 A | 10/1994 | Capon et al. | 536/23.4 |
| 5,371,010 A | 12/1994 | Brown et al. | 435/397 |
| 5,397,706 A | * 3/1995 | Correa et al. | 435/406 |
| 5,405,772 A | * 4/1995 | Ponting | 435/378 |
| 5,472,867 A | 12/1995 | Kanz et al. | 435/385 |
| 5,474,931 A | 12/1995 | DiSorbo et al. | 435/407 |
| 5,556,954 A | * 9/1996 | Burn et al. | 536/24.1 |
| 5,573,937 A | 11/1996 | Shinmoto et al. | 435/383 |
| 5,599,705 A | * 2/1997 | Cameron | 435/378 |
| 5,766,951 A | 6/1998 | Brown et al. | 435/407 |
| 5,945,337 A | 8/1999 | Brown et al. | 435/389 |

FOREIGN PATENT DOCUMENTS

| | | |
|---|---|---|
| WO | WO 92/05246 | 4/1992 |
| WO | WO 92/18615 | 10/1992 |
| WO | WO 95/02685 | 1/1995 |
| WO | WO 96/39487 | 12/1996 |
| WO | WO 97/34999 | 9/1997 |

OTHER PUBLICATIONS

Steen et al. c–Kit ligand combined with GM–CSF and/or IL–3 can expand CD34+ hematopoietic progenitor subsets for several weeks in vitro. Stem Cells 12:214–224, 1994.*
Haylock et al. Ex vivo expansion and maturation of peripheral blood CD34+ cells into the myeloid lineage. Blood 80(6):1405–1412, 1992.*
Civin CI Human monomyeloid cell membrane antigens. Exp. Hematol. 18:461–467, 1990.*
Freshney RI Culture of animal cells: A manual of basic technique. 2nd ed., Alan R. Liss, Inc., New York, pp. 80–81, 1987.*
GIBCO BRL Life Technologies 1993–1994 Catalogue and Reference Guide, pp. 1–38, 1–82, Life Technologies, Inc. Gaithersburg, MD, 1993.*
Kohn et al. Engraftment of gene–modified umbilical cord blood cells in neonates with adenosine deaminase deficiency. Nature Medicine 1(10):1017–1023, 1995.*
Traycoff, C.M., et al., "Rapid exit from $G_1/G_0$ phases of cell cycle in response to stem cell factor confers on umbilical cord blood CD34$^{30}$ cells an enhanced ex vivo expansion potential," *Hematology* 22:1264–1272 (1994).
Eaves, C.J. et al., "Methodology of Long–Term Culture of Human Hemopoietic Cells," *J. Tiss. Cult. Meth.* 13(1):55–62 (1991).
GIBCO BRL Life Technologies™ 1993–1994 Catalogue and Reference Guide, pp. 1–38, 1–54, 1–70, 1–99, 1–116, 4–43, 4–44, 4–45, 4–46, 4–59, and 4–63, Life Technologies™, Inc., Gaithersburg, MD (1993).
Greenberg, H.M. et al., "Human Granulocytes Generated in Continuous Bone Marrow Culture are Physiologically Normal," *Blood* 58 54(4):724–732 (1981).
Zang, M., et al., "Production of Recombinant Proteins in Chinese Hamster Ovary Cells Using A Protein–Free Cell Culture Medium," *Bio/Technology* 13:389–392 (Apr. 1995).
Life Technologies 1993–1994 Catalogue and Reference Guide, pp. 1–2, 1–34, 1–82, 4–43, 5–3 and 5–4 (1993).

(List continued on next page.)

Primary Examiner—Anne-Marie Falk
(74) Attorney, Agent, or Firm—Sterne, Kessler, Goldstein & Fox P.L.L.C.

(57) ABSTRACT

The present invention provides a serum-free supplement which supports the growth of hematopoietic cells in culture. Also provided are a medium comprising a basal medium supplemented with the serum-free supplement of the present invention. The present invention also provides methods for culturing and for differentiating hematopoietic cells.

58 Claims, 15 Drawing Sheets

OTHER PUBLICATIONS

PCT Gazette, International Bureau of the World Intellectual Property Organization Under the Patent Cooporation Treaty, pub., p. 275 (Jan. 1998).

Sonoda, Y. et al., "Analysis in serum–free culture of the targets of recombinant human hemopoietic growth factors: Interleukin 3 and granulocyte/macrophage–colony–stimulating factor are specific for early developmental stages," *Proc. Natl. Acad. Sci. USA* 85(12):4360–4364 (1988).

Ham, R.G., "Clonal Growth of Mammalian Cells in a Chemically Defined, Synthetic Medium," *Proc. N.A.S.* 53(2):288–293 (Feb. 1965).

Ham, R.G., "Formulation of Basal Nutrient Media," *Methods for Preparation of Media, Supplements, and Substrata for Serum–Free Animal Cell Culture*, Alan R. Liss, Inc., publ., New York, pp. 3–21 (1984).

Casadevall, N. et al., "Erythroid Progenitors in Polycythemia Vera: Demonstration of Their Hypersensitivity to Erthropoietin Using Serum Free Cultures," *Blood* 59(2):447–451 (1982).

Eliason, J.F. and Odartchenko, N., "Colony formation by primitive hemopoietic progenitor cells in serum–free medium," *Proc. Natl. Acad. Sci. USA* 82(3):775–779 (1985).

Maurer, H.R., "Towards Chemically–defined, Serum–free Media for Mammalian Cell Culture," in: *Animal cell culture: a practical approach*, Freshney, R.I., Ed., IRL Press, Oxford, publ., pp. 13–31 (1986).

Bradley, T.R. and Metcalf, D., "The Growth of Mouse Bone Marrow Cells In Vitro," *Aust. J. Exp. Biol. Med. Sci.* 44:287–300 (1966).

Collins, P.C. et al., "Ex vivo culture systems for hematopoietic cells," *Curr. Opin. Biotech.* 7(2):223–230 (Apr. 1996).

Daley, J.P. et al., "Ex Vivo Expansion of Human Hematopoietic Progenitor Cells in Serum–Free StemPro™ Medium," *Focus* 18(3):62–67 (Oct. 12, 1996).

Daniel C.P. and Exter, T.M., "The role of growth factors in haemopoietic development: Clinical and biological implications," *Cancer and Metastasis Rev.* 8(3):253–262 (1989).

de Wynter et al., "Comparison of Purity and Enrichment of CD34+ Cells from Bone Marrow, Umbilical Cord and Peripheral Blood (Primed for Apheresis) Using Five Separation Systems," *Stem Cells* 13(5):524–532 (Sep. 1995).

Dexter, T.M. et al., "Conditions Controlling the Proliferation of Haemopoietic Stem Cells In Vitro," *J. Cell. Physiol.* 91(3):335–344 (1977).

Haylock, D.M. et al., "Ex Vivo Expansion and Maturation of Perimperal Blood $CD34^{30}$ cells into the Myeloid Lineage," *Blood.* 80(6):1405–1412 (1992).

International Search Report issued by PCT International Searching Authority for Application No. PCT/US97/01867. Mailing Date: Jun. 5, 1997.

Koller, M.R. and Palsson, B.O., "Tissue Engineering: Reconstitution of Human Hematopoiesis Ex Vivo," *Biotech. Bioeng.* 42(8):909–930 (1993).

Lambert, K.J. and Birch, J.R., "Cell Growth Media," in: *Animal Cell Biotechnology vol. 1*, Spier, R.E. and Griffiths, J.B., eds., Academic Press, pp. 85–123 (1985).

McAdams, T.A. et al., "Hematopoietic cell culture therapies (Part 1): cell culture consideration," *TIBTECH* 14(9):341–349 (Sep. 1996).

Migliaccio, G. and Migliaccio, A.R., "Serum–Deprived Cultures of Primary Hematopoietic Cells," in *Culture of Specialized Cells: Culture of Hematopoietic Cells*, Freshney, R.I. et al., eds., Wiley–Liss, Inc, pp. 81–98 (1994).

Migliaccio, G. et al., "The Biology of Hematopoietic Growth Factors: Studies of in vitro under Serum–deprived Conditions," *Exp. Hematol.* 18(9):1049–1055 (1990).

Sandstrom, C.E. et al. "Review: Serum–Free Media for Cultures of Primitive and Mature Hematopoietic Cells," *Biotech. Bioeng.* 43(8):706–733 (1994).

Sigma' Chemical Company Catalog, Tissue Culture Media and Reagents, pp. 1442, 1470, and 1475, Sigma' Chemical Co., St. Louis, MO (1989).

Sigma® Chemical Company Catalog, Tissue Culture Media and Reagents, pp. 1495, 1512, 1514, and 1516, Sigma® Chemical Co., St. Louis, MO (1994).

"StemPro™–34 SFM," *Spectrum*, Life Technologies, Inc., p. 12 (May 12, 1996).

* cited by examiner

HEMATOPOIETIC CELL CULTURE NUTRIENT SUPPLEMENT

CROSS REFERENCE TO RELATED APPLICATIONS

This application claims priority to U.S. provisional application No. 60/013,149, filed Mar. 12, 1996.

FIELD OF THE INVENTION

The present invention relates to a replacement for the serum supplementation normally required for ex vivo expansion of $CD34^+$ hematopoietic cells and cells of myeloid lineage.

BACKGROUND OF THE INVENTION

Blood cells in the mammal can be divided into three main categories or families: red cells, white cells of myeloid lineage, and white cells of the lymphocytic lineage. Red blood cells carry oxygen from the lungs to the tissues and cells of the body and transport $CO_2$ from the tissues and cells back to the lungs for elimination. White cells of myeloid lineage include: neutrophils, basophils, eosinophils, megakaryocytes, monocytes/macrophages, and dendritic cells. These cells play a role in the identification and elimination of foreign organisms (e.g. bacteria) or damaged tissue, cells and substances from the body. White cells of lymphocytic lineage are divided into two main subgroups: T lymphocytes (helper cells, killer cells, suppressor cells), which are involved in cell mediated responses to viruses, tumor cells and foreign tissue grafts; and B lymphocytes, which are involved in the production of antibodies which circulate in the blood and react in a chemically specific fashion to foreign materials (e.g. bacteria, foreign proteins).

Embryologically, blood cells are formed in the third week of development from cells of the splanchnic mesoderm (Langman, J., *Medical Embryology*, 3rd ed., pp. 1–7, Williams and Wilkins Co., Baltimore, Md., 1975). In the yolk sac, hematopoiesis (i.e., blood cell formation) initially occurs in clusters or islands ("blood islands") of splanchic mesoderm cells. The blood islands then migrate to the liver during fetal development. At full gestation and immediately after delivery, these cells migrate to the bone marrow in the shafts of long bones, ribs, and hips. Throughout the remainder of life, the bone marrow serves as the normal site of blood cell formation, releasing mature cells into the circulation (Wintrobe, M. M., *Clinical Hematology*, pp. 1–7, Lea and Febiger, Philadelphia, Pa., 1967).

Hematopoiesis is an ordered process by which different blood cells are produced at a rate of 400 billion per day (Koller, M. R. and Palsson, B. O., *Ex Vivo* 42:909–930 (1993)). Since the early 1960s, researchers have acquired experimental evidence for the hypothesis that each of the various blood cell types are derived from a common "pluripotent" stem cell in the mouse (Till, J. E. and McCulloch, E. A., *Radiation Res.* 14:213–222 (1961); Becker, A. J. et al., *Nature* 195:452–454 (1963); Siminovitch, L. et al., *J. Cell. Comp. Physiol.* 62:327–336 (1963)). Experimental evidence also supports the existence of pluripotent stem cells in humans (Nowell, P. C. and Hungerford, D. A., *J. Natl. Cancer Inst.* 25:85-109 (1960); Tough, I. M. et al., *Lancet* 1:411–417 (1961); Barr, R. D. and Watt, I., *Acta Haemat.* 60:29–35 (1978)).

Hematopoietic cell differentiation occurs in stages (Pimentel, E., Ed., *Handbook of Growth Factors Vol. III: Hematopoietic Growth Factors and Cytokines*, pp. 1–2, CRC Press, Boca Raton, Fla., 1994). The first stage is represented by the hematopoietic stem cell. Development then diverges along the lymphoid and myeloid lineages as lymphoid progenitor cells and myeloid/erythroid progenitor cells are formed. Development further diverges within each of these lineages. Lymphoid progenitor cells form pre-B and pre-T precursor cells, which subsequently develop into B lymphocytes and T lymphocytes, respectively. Myeloid/erythroid progenitor cells form (1) erythroid burst-forming unit (BFU-E) cells, which eventually develop into erythrocytes; (2) megakaryocyte colony-forming unit (CFU-MEG) cells, which eventually develop into megakaryocytes and platelets; (3) granulocyte/macrophage colony-forming units (CFU-GM), which eventually develop into monocytes, macrophages, and neutrophils; (4) eosinophils; and (5) basophils.

A major focus in the field of experimental hematology continues to be the identification of the most primitive, pluripotent stem cell. One approach has been to identify cell surface markers (such as CD antigens) on the surface of progenitor cells and to correlate these markers with stages of development or differentiation by the cells' ability to form colonies of differentiated cells in methylcellulose culture systems. CD antigen expression has been shown to be modulated during cellular differentiation (Sieff, C. et al., *Blood* 60:703 (1982)). Hematopoietic stem cells are $CD34^+$ cells. That is, they express the CD34 surface marker. The most primitive known human progenitor cell, which has been characterized as $CD34^+/CD33^-CD38^-$, represents only 1 to 2% of all bone marrow cells (Civin, C. I. et al., *J. Immunol.* 133:157 (1984)).

In the mid 1960's, in order to better understand the mechanisms of normal and aberrant hematopoiesis, investigators began trying to grow bone marrow cells ex vivo using both suspension and semi-solid tissue culture systems. The early studies of Bradley and Metcalf (Bradley, T. R. and Metcalf, D., *Biol Med. Sci.* 44:287–300 (1966)), as well as those of Pluznik and Sachs (Pluznik, D. H. and Sachs, L., *Expl. Cell Res.* 43:553–563 (1966)), demonstrated that serum alone was not sufficient to support the growth of myeloid progenitors in culture. Cell growth required the presence of factor(s), secreted by other cells (i.e. feeder cells) and found in the conditioned media from cultures of these cells. It is now clear that the growth of hematopoietic tissue ex vivo requires the presence of several cytokines or hematopoietic growth factors.

Several distinct factors have been identified, cloned and are now routinely manufactured as recombinant molecules for both research and/or clinical use. These include erythropoietin (Lin, F. K. et al., *Proc. Natl. Acad. Sci. U.S.A.* 82:7580–7584 (1985); Stone, W. J. et al., *Am. J. Med. Sci* 296:171–179 (1988)), interleukin-3 (IL-3) (Fung, M. C. et al., *Nature* 307(5948):233–237 (1984); Yokota, T. et al., *Proc. Natl. Acad. Sci. U.S.A.* 81:1070–1074 (1984); Ganaser, A. et al., *Blood* 76:666–676 (1990)), granulocyte macrophage-colony stimulating factor (GM-CSF) (Wong, G. G. et al., *Science* 228:810–815 (1985); Sieff, C. A. et al., *Science* 230:1171–1173 (1985)); granulocyte-colony stimulating factor (G-CSF) (Souza, L. M. et al., *Science* 232:61–65 (1986)); stem cell factor (SCF) (Copeland, N. G. et al., *Cell.* 63:175–183 (1990); Flanagan, J. G. et al., *Cell* 63:185–194 (1990); Zsebo, K. M. et al., Cell 63:195–201 (1990); Martin, F. H. et al., *Cell* 63:203–211 (1990); Szebo, K. M. et. al., *Cell* 63:213–224 (1990); Huang, E. et al., *Cell* 63:225–233 (1990)), and interleukin-11 (Il-11) (Paul, W. et al., *Proc. Natl. Acad. Sci. U.S.A* 87:7512–7516 (1990)), to cite only a few.

In 1977, Dexter and his colleagues developed a long-term bone marrow culture (LTBMC) protocol (Dexter, T. M. et al., *J. Cell Physiol.* 91:335–344 (1977)). Known as "Dexter" culture, this type of cell culture system does not require the use of conditioned media and appears to establish and mimic, in vitro, the hematopoietic environment. Long term cultures have been established using human bone marrow (Grenberger, H. M. et al., *Blood* 58:724–732 (1981); Eaves, C. J. et al., *J. Tiss. Cult. Method.* 13:55–62 (1991)), as well as the marrow from other animal species (Eastment, C. E. and Ruscetti, F. W., Evolution of Hematopoiesis in Long-Term Bone Marrow Culture: Comparison of Species Differences, in: *Long-Term Bone Marrow Cultures, Droc Foundation Series* 18, pp. 97–118, Allan R. Liss, Inc., New York, N.Y., 1984).

In long-term culture systems, growth and differentiation of stem cells and early progenitor cells appears to require either direct cell to cell contact or very close proximity between the developing hematopoietic cells and stromal cells (Dexter, T. M. et al., *J. Cell. Physiol.* 91:335–344 (1977)).

Each of the above cell culture systems (e.g., liquid static culture, semi-solid culture and long term bone marrow culture) appears to have their own unique, critical requirements which must be met before one can culture hematopoietic cells of human or other mammalian species. To date, however, a common requirement, and major disadvantage, of cell culture systems has been the requirement for undefined components contained in animal sera (e.g., fetal bovine serum or horse serum) or in "conditioned cell culture media" for optimal growth.

The use of serum in the culture of hematopoietic cells is disadvantageous for several reasons. Serum is a major source of undefined differentiation factors and thus tends to promote hematopoietic cell differentiation, rather than expansion. The efficiency of serum varies between lots of serum. Some lots of serum have been found to be toxic to cells. Moreover, serum may be contaminated with infectious agents such as mycoplasma, bacteriophage, and viruses. Finally, because serum is an undefined and variable component of a medium to which serum is added, the use of serum prevents the true definition and elucidation of the nutritional and hormonal requirements of the cultured cells.

In view of the many problems associated with the use of serum in the growth of CD34$^+$ hematopoietic cells, laboratories performing work with CD34$^+$ hematopoietic cells must resort to pre-screening serum prior to purchase. However, the pre-screening process is time-consuming and subject to interpretation. Even after a satisfactory lot is identified, storage of large quantities of pre-screened lots of serum at –20° C. and below is problematic.

As a result, researchers have attempted to replace animal sera or conditioned media with serum-free culture media of varying degrees of chemical definition. These attempts have met with varying degrees of success, depending upon the identity of the cell type one is trying to culture. The development of serum-free media has recently been reviewed (Sandstrom, E. E. et al., *Biotech. & Bioengin.* 43:706–733 (1994); Collins, P. C. et al., *Curr. Opin. Biotech.* 7:223–230 (1996); McAdams, T. A. et al., *TIBTECH* 14:341–349 (1996)).

International Patent Application WO 96/39487 discloses a serum-free medium for culturing human mesenchymal precursor cells. U.S. Pat. No. 5,405,772 discloses a serum-free or serum-depleted medium for culturing hematopoietic cells and bone marrow stromal cells. U.S. Pat. No. 4,972,762 discloses a serum-free medium, containing penicillamine and N-acetylcysteine, for growing hybridomas and lymphoid cells.

Research with CD34$^+$ hematopoietic cells, cultivation of CD34$^+$ hematopoietic cells in culture, expansion of CD34$^+$ hematopoietic cells, control of differentiation of CD34$^+$ hematopoietic cells, and explantation of CD34$^+$ hematopoietic cells, is hindered by the necessity for serum. Further, a major problem associated with previously available serum-free media is short shelf-life. Oxidation of the vitamins and lipid ingredients of serum-free media occurs during storage. CD34$^+$ hematopoietic cell growth and expansion cannot be sustained in a serum-free medium which contains oxidated ingredients. Thus, there remains a need for a serum-free medium supplement and a serum-free medium which supports the growth and expansion of CD34$^+$ hematopoietic cells and which can be stored for long periods of time.

SUMMARY OF THE INVENTION

The present invention provides a serum-free, eukaryotic cell culture medium supplement comprising or obtained by combining one or more ingredients selected from the group consisting of one or more antioxidants, one or more albumins or albumin substitutes, one or more lipid agents, one or more insulins or insulin substitutes, one or more transferrins or transferrin substitutes, one or more trace elements, and one or more glucocorticoids, wherein a basal cell culture medium supplemented with the supplement is capable of supporting the expansion of CD34$^+$ hematopoietic cells and cells of myeloid lineage, in serum-free culture.

The present invention also provides a serum-free, eukaryotic cell culture medium supplement comprising or obtained by combining one or more antioxidants and one or more ingredients selected from the group consisting of one or more albumins or albumin substitutes, one or more lipid agents, one or more insulins or insulin substitutes, one or more transferrins or transferrin substitutes, one or more trace elements, and one or more glucocorticoids, wherein a basal cell culture medium supplemented with the supplement is capable of supporting the expansion of CD34$^+$ hematopoietic cells and cells of myeloid lineage, in serum-free culture.

The present invention also specifically provides a serum-free, eukaryotic cell culture medium supplement comprising or obtained by combining one or more ingredients selected from the group consisting of N-acetyl-L cysteine, human serum albumin, the product soluble human lipids for serum-free media, sold under the trademark HUMAN EX-CYTE® (Bayer Corporation, Kankakee Ill., ethanolamine HCl, human zinc insulin, human iron saturated transferrin, Se$^{4+}$, hydrocortisone, D,L-tocopherol acetate, and 2-mercaptoethanol, wherein the ingredients are present in an amount which, when the supplement is added to a basal cell culture medium, supports the expansion of CD34$^+$ hematopoietic cells and cells and cells of myeloid lineage, in serum-free culture.

The present invention also provides a method of making a serum-free, eukaryotic cell culture medium supplement, the method comprising admixing the ingredients of the supplement of the invention in any order. The invention specifically comprises admixing water, N-acetyl-L-cysteine, human serum albumin, the product soluble human lipids for serum-free media, sold under the trademark HUMAN EX-CYTE®, ethanolamine HCl, zinc insulin, human iron saturated transferrin, a Se$^{4+}$ salt, hydrocortisone, D,L-tocopherol acetate, and 2-mercaptoethanol.

The present invention also provides a method of making a serum-free, eukaryotic cell culture medium supplement, the method comprising admixing water, N-acetyl-L cysteine, human serum albumin, the product soluble human lipids for serum-free media, sold under the trademark HUMAN EX-CYTE®, ethanolamine HCl, human zinc insulin, human iron saturated transferrin, a $Se^{4+}$ salt, hydrocortisone, D,L-tocopherol acetate, and. 2-mercaptoethanol, wherein each ingredient is present in an amount which, when added to a basal medium, supports the expansion of $CD34^+$ hematopoietic cells and cells of myeloid lineage, in serum-free culture.

The present invention also provides a kit comprising a carrier means, the carrier means being compartmentalized to receive in close confinement therein one or more container means, wherein a first container means contains the supplement of the present invention, and wherein optionally a second container means contains a basal medium.

The present invention also provides a serum-free eukaryotic cell culture medium comprising a basal cell culture medium supplemented with the serum-free culture supplement of the invention, wherein the supplemented culture medium is capable of supporting the expansion of $CD34^+$ hematopoietic cells and cells of myeloid lineage, in serum-free culture.

The present invention also provides a serum-free eukaryotic cell culture medium obtained by combining a basal cell culture medium with the serum-free supplement of the invention, wherein the medium is capable of supporting the expansion of $CD34^+$ hematopoietic cells and cells of myeloid lineage, in serum-free culture.

The present invention also provides a method of making a serum-free eukaryotic cell culture medium, the method comprising admixing a basal cell culture medium with the serum-free supplement of the invention, wherein the medium is capable of supporting the expansion of $CD34^+$ hematopoietic cells and cells of myeloid lineage, in serum-free culture.

The present invention also provides a serum-free eukaryotic cell culture medium comprising one or more ingredients selected from the group consisting of one or more antioxidants, one or more albumins or albumin substitutes, one or more lipid agents one or more insulins or insulin substitutes, one or more transferrins or transferrin substitutes, one or more trace elements, one or more glucocorticoids, one or more inorganic salts, one or more energy sources, one or more buffering agents, one or more pyruvate salts, one or more pH indicators, one or more amino acids, and one or more vitamins, wherein the medium is capable of supporting the expansion of $CD34^+$ hematopoietic cells and cells of myeloid lineage in serum-free culture.

The present invention specifically provides a serum-free, eukaryotic cell culture medium comprising the ingredients N-acetyl-L-cysteine, 2-mercaptoethanol, human serum albumin, D,L-tocopherol acetate, the product soluble human lipids for serum-free media, sold under the trademark HUMAN EX-CYTE®, ethanolamine, human zinc insulin, iron-saturated transferrin, $Se^{4+}$, hydrocortisone, $Ca^{2+}$, $K^+$, $Mg^{2+}$, $Na^+$, $CO_3^{2-}$; $PO_4^{3-}$; D-glucose, HEPES buffer, sodium pyruvate, phenol red, glycine, L-alanine, L-asparagine, L-cysteine, L-aspartic acid, L-glutamic acid, L-phenylalanine, L-histidine, L-isoleucine, L-lysine, L-leucine, L-glutamine, L-arginine HCL, L-methionine, L-proline, L-hydroxyproline, L-serine, L-threonine, L-tryptophan, L-tyrosine, and L-valine, biotin, D-calcium pantothenate, choline chloride, folic acid, i-inositol, niacinamide, pyridoxal HCl, riboflavin, thiamine HCl, and vitamin $B_{12}$. The present invention also provides a method of making the medium of the present invention, the method comprising admixing the ingredients of the medium.

The present invention also provides a serum-free, eukaryotic cell culture medium obtained by combining the ingredients water, N-acetyl-L-cysteine, 2-mercaptoethanol, human serum albumin, D,L-tocopherol acetate, the product soluble human lipids for serum-free media, sold under the trademark HUMAN EX-CYTE®, ethanolamine, human zinc insulin, iron-saturated transferrin, a $Se^{4+}$ salt, hydrocortisone, a calcium salt, a potassium salt, a magnesium salt, a sodium salt, a carbonate salt, a phosphate salt, D-glucose, HEPES, a pyruvate salt, phenol red, glycine, L-alanine, L-asparagine, L-cysteine, L-aspartic acid, L-glutamic acid, L-phenylalanine, L-histidine, L-isoleucine, L-lysine, L-leucine, L-glutamine, L-arginine HCL, L-methionine, L-proline, L-hydroxyproline, L-serine, L-threonine, L-tryptophan, L-tyrosine, and L-valine, biotin, D-calcium pantothenate, choline chloride, folic acid, i-inositol, niacinamide, pyridoxal HCl, riboflavin, thiamine HCl, and vitamin $B_{12}$, wherein the ingredients are present in an amount which supports the expansion of $CD34^+$ hematopoietic cells and cells of myeloid lineage.

The present invention provides a method of making a serum-free, eukaryotic cell culture medium said method comprising admixing the ingredients water, N-acetyl-L-cysteine, 2-mercaptoethanol, human serum albumin, D,L-tocopherol acetate, the product soluble human lipids for serum-free_media, sold under the trademark HUMAN EX-CYTE®, ethanolamine, human zinc insulin, iron-saturated transferrin, a $Se^{4+}$ salt, hydrocortisone, a calcium salt, $CaCl_2$, one or more potassium salts, a magnesium salt, a sodium salt, a carbonate salt, a phosphate salt, D-glucose, HEPES, a pyruvate salt, phenol red, glycine, L-alanine, L-asparagine, L-cysteine, L-aspartic acid, L-glutamic acid, L-phenylalanine, L-histidine, L-isoleucine, L-lysine, L-leucine, L-glutamine, L-arginine HCL, L-methionine, L-proline, L-hydroxyproline, L-serine, L-threonine, L-tryptophan, L-tyrosine, and L-valine, biotin, D-calcium pantothenate, choline chloride, folic acid, i-inositol, niacinamide, pyridoxal HCl, riboflavin, thiamine HCl, and vitamin $B_{12}$, wherein the ingredients are present in an amount which supports the expansion of $CD34^+$ hematopoietic cells and cells of myeloid lineage.

The present invention also provides a composition comprising $CD34^+$ hematopoietic cells and the serum-free medium of the present invention, wherein the serum-free medium is capable of supporting the expansion of $CD34^+$ hematopoietic cells and cells of myeloid lineage in serum-free culture.

The present invention also provides a method of expanding $CD34^+$ hematopoietic cells and cells of myeloid lineage, the method comprising contacting cells with the medium of the present invention and culturing the cells under serum-free conditions suitable to facilitate the expansion of the cells.

The present invention also provides a method of providing $CD34^+$ hematopoietic cells to a mammal, the method comprising contacting $CD34^+$ hematopoietic cells with the medium of the present invention, cultivating cells under conditions suitable to facilitate the expansion of the cells in serum-free culture, and introducing the expanded cells into a mammal.

The present invention also provides a method of causing $CD34^+$ hematopoietic cells to differentiate into a particular type of cell in serum-free culture, the method comprising contacting CD34+ hematopoietic cells with the medium of the present invention, cultivating the cells under conditions suitable to facilitate the expansion of cells in serum-free culture, and adding one or more differentiation factors or changing culturing conditions to induce differentiation of cells to form a different type of hematopoietic cell.

The present invention also provides a method of providing differentiated hematopoietic cells to a mammal, the method comprising contacting CD34+ hematopoietic cells with the medium of the present invention, cultivating the cells under conditions suitable to facilitate the expansion of the cells in serum-free culture, adding one or more differentiation factors or changing culturing conditions to induce differentiation of cells to form a different type of hematopoietic cell, and introducing the differentiated cells into a mammal.

The present invention also provides a method of expanding recombinant CD34+ hematopoietic cells, the method comprising obtaining a recombinant CD34+ hematopoietic cell containing a nucleic acid molecule which encodes a protein of interest, and culturing the cell in the medium of the present invention to form a population of recombinant cells.

The present invention also provides a method of providing a recombinant CD34+ hematopoietic cell to a mammal, the method comprising obtaining a recombinant CD34+ hematopoietic cell containing a nucleic acid molecule which encodes a protein of interest, culturing the cell in the medium of the present invention to form a population of recombinant CD34+ hematopoietic stem cells, and introducing the recombinant cells into a mammal.

The invention also relates to a method for regeneration of a eukaryotic cell culture medium (preferably a serum-free medium) comprising mixing a sufficient amount of an antioxidant (preferably N-acetyl-L-cysteine or a derivative thereof) to generate the medium. After regeneration, the medium may be used to support growth of any eukaryotic cell, particularly CD34+ hematopoietic cells.

The invention also relates to increasing or enhancing shelf-life of a eukaryotic cell culture medium (preferably a serum-free medium) comprising mixing the medium with a sufficient amount of an antioxidant (preferably N-acetyl-L-cysteine or a derivative thereof) to increase or enhance the shelf-life of the medium.

DETAILED DESCRIPTION OF THE PREFERRED EMBODIMENTS

Figure 1:
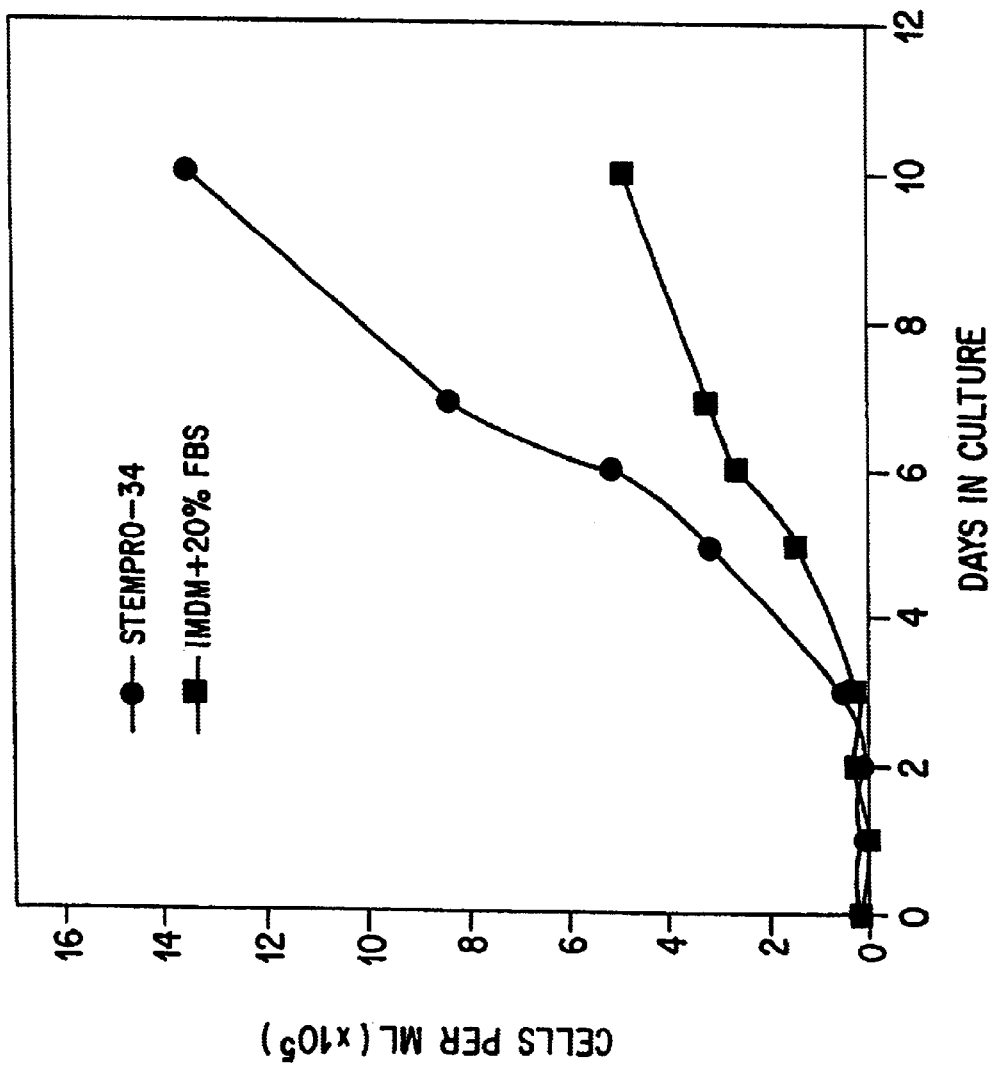
FIG. 1 shows the effect of the serum-free StemPro-34™ medium on the kinetics of growth factor driven expansion of an enriched population of CD34+ hematopoietic cells, as compared to the effect of serum.

The present invention provides a chemically defined cell culture supplement and medium which has been developed specifically for stem cells and progenitor cells of the hematopoietic system. This formulation is unique in its ability to support the expansion of CD34+ cells which are, at the present time, defined as the earliest hematopoietic stem cell identifiable in bone marrow, peripheral blood or neonatal cord blood. The supplement and the medium of the present invention are particularly suited for supporting the expansion of CD34+ cells and cells of myeloid lineage, including BFU-E cells, erythrocytes, CFU-MEG cells, megakaryocytes, CFU-GM cells, monocytes, macrophages, neutrophils eosinophils, and basophils. In earlier stages of development, cells of myeloid lineage express the CD34+ marker protein. In later stages of development, cells of myeloid lineage do not express detectable levels of the CD34+ marker protein. Whether a cell of myeloid lineage expresses the CD34+ marker protein can be determined by one of ordinary skill in the art using well-known techniques, such as fluorescence activated cell sorting.

The supplement and the medium of the present invention can also be used to culture or expand cells of mesenchymal origin. Such cells include but are not limited to, chondrocytes, osteoclasts, osteoblasts, and epithelial cells of skin and vascular tissue. The supplement and the medium of the present invention can also be used to culture both primary and immortalized cells of most or all embryonic origin (e.g., ectodermal derivatives, mesodermal derivatives, and endodermal derivatives). These cells include cells of the central and peripheral nervous system (neurons, glial cells, and astrocytes), epithelial cells (sensory epithelial cells, epidermal cells (skin, mammary, hair, nails, pituitary gland, sebaceous gland)), connective tissue cells (cartilage, bone, striated and smooth muscle, hematopoietic cells, lymphoid cells, kidney, gonadal cells, adrenal cells) and parenchymal cells of the liver, pancreas, thyroid, thymus, as well as epithelial linings of the urinary bladder, urethra, tympanic cavity, and eustachian tube. These cells can be of human or other mammalian or eukaryotic origin.

Using the serum-free supplement or medium of the present invention, the growth, expansion, and differentiation of hematopoietic cells can be regulated by the addition of defined growth factors or other cytokines. Such influence over hematopoietic cells in culture is not possible when cells are cultured in serum-supplemented media. Undefined components in serum obscure the cellular responses to defined factors. Using the supplement or the medium of the present invention, CD34$^+$ hematopoietic cells (including hematopoietic stem cells), and cells of myeloid lineage can be expanded and differentiated in suspension culture and in the absence of stromal cells, collagen, or support matrices.

Stromal cells are bone marrow cells which form a supporting network for hematopoietic cells in vivo and in vitro. Stromal cells serve as sites of attachment for hematopoietic cells. Further, stromal cells secrete cytokines and other growth factors which hematopoietic cells require for expansion and growth. In culture, stromal cells form an adherent layer and include endothelial cells, macrophages, fibroblasts, and adipocytes. Using the supplement or the medium of the present invention, it is not necessary to co-culture hematopoietic cells with stromal cells in order to expand the hematopoietic cell population.

The serum-free supplement and the medium of the present invention differ from previously available serum-free media in that the supplement and medium of the present invention provide for the growth and expansion of both the putative pluripotent stem cell population (i e., CD34$^+$ cells from bone marrow, peripheral blood and neonatal cord blood) and differentiated progeny.

The serum-free supplement and the medium of the present invention can be used to culture hematopoietic cells derived from a number of animals, including human, monkey, ape, mouse, rat, hamster, rabbit, guinea pig, cow, swine, dog, horse, cat, goat, and sheep. Preferably, human hematopoietic cells are cultured.

The supplement and the medium of the present invention allow hematopoietic stem cells and their progeny to respond fully to human recombinant hematopoietic growth factors or other cytokines. Until now, the cellular response to defined growth factors has been hindered by undefined components in serum and the lack of hematopoietic cell-specific optimization of the media chemistry. Unlike other serum-free media, the supplement and the medium of the present invention include an antioxidant or combination of antioxidants which protect hematopoietic cells from the detrimental (and often lethal) effects of multiple free radical species and other toxic moieties known to be generated in the cell culture environment. Thus, by addition of antioxidants according to the invention, shelf-life of a medium can be increased or enhanced. Moreover, to the extent that such detrimental products are formed during the storage of a medium, addition of antioxidants according to the invention provide for regeneration of the medium, thereby enhancing or increasing the capacity or the ability of the medium to expand cells. The addition of antioxidants to achieve such beneficial results can be applied to any cell culture media, particularly serum-free media. Examples of the media which can be used include media for expansion both primary and immortalized cells of most or all embryonic origin (see infra). Such media include, but are not limited to DMEM, Ham's F-10, Ham's F-12, MCDB series, AIM-5, Keratinocyte SFM, chemically defined keratinocyte media, AmnioMax, human chondrocyte media, human dermal fibroblast media, CHO II, CHO III (GibcoBRL).

In the description that follows, a number of terms conventionally used in the field of cell culture media and for the growth of eukaryotic cells are utilized extensively. In order to provide a clear and consistent understanding of the specification and claims, and the scope to be given such terms, the following definitions are provided.

The term "regeneration" refers to increasing the ability or capacity of a medium to expand eukaryotic cells. Typically, eukaryotic cell culture media, particularly serum-free media will, upon storage, lose or have reduced ability or capacity to support growth or expansion of cells. In determining the capacity or ability of a medium to grow or expand cells has been increased, comparisons can be made between a medium supplemented with an antioxidant and a control lacking the antioxidant. According to the invention, the capacity or ability of a medium to facilitate the growth or expansion of cells is enhanced or increased if the medium containing the antioxidant facilitates a greater level of growth or expansion than a medium which does not contain the antioxidant.

The term "shelf-life" refers to the storage over time of medium. Typically, media are stored at 4° to 25° C., although other storage temperatures may be used. In determining if a shelf-life has been enhanced or increased, comparisons can be made to evaluate the effect of storage on capacity or ability of a particular medium to support cell growth or expansion. According to the invention, the shelf-life is said to be enhanced or increased if the stored medium containing the antioxidant outperforms a control medium, which does not contain the antioxidant and which is stored for the same period of time as the medium which contains the antioxidant. Performance is determined by comparing the level of cell growth or expansion to the level in medium containing the antioxidant and the control medium.

The term "albumin substitute" refers to any compound which may be used in place of human serum albumin (e.g., bovine serum albumin (BSA) or the product lipid-rich bovine serum albumin for cell culture, sold under the trademark ALBUMAX®I (Life Technologies, Gaithersburg, Md.) in the supplement of the invention to give substantially similar results as albumin. Albumin substitutes may be any protein or polypeptide source. Examples of such protein or polypeptide samples include but are not limited to bovine pituitary extract, plant hydrolysate (e.g., rice hydrolysate), fetal calf albumin (fetuin), egg albumin, human serum albumin (HSA), or another animal-derived albumins, chick extract, bovine embryo extract, the product lipid-rich bovine serum albumin for cell culture, sold under the trademark ALBUMAX®I, and the product lipid-rich bovine serum albumin for cell culture, sold under the trademark ALBUMAX II® (Life Technologies, Gaithersburg, Md.).

Preferably, the albumin is of human origin. Most preferably, the albumin is human serum albumin. In the supplement and the medium of the present invention, the concentration of albumin or albumin substitute which facilitates cell growth, expansion, and differentiation in culture can be determined using only routine experimentation.

The term "transferrin substitute" refers to any compound which may replace transferrin in the supplement of the invention to give substantially similar results as transferrin. Examples of transferrin substitutes include but are not limited to any iron chelate compound. Iron chelate compounds which may be used include but are not limited to iron chelates of ethylenediaminetetraacetic acid (EDTA), ethylene glycol-bis(β-aminoethyl ether)-N,N,N',N'-tetraacetic acid (EGTA), deferoxamine mesylate, dimercaptopropanol, diethylenetriamine-pentaacetic acid (DPTA), and trans-1,2-diaminocyclohexane-N,N,N',N'-tetraacetic adic (CDTA), as well as a ferric citrate chelate and a ferrous sulfate chelate.

Preferably, the transferrin is iron saturated transferrin. Most preferably, the transferrin is iron saturated human transferrin. In the supplement and the medium of the present invention, the concentration of the transferrin or transferrin substitute which facilitates cell growth, expansion, and differentiation in culture can be determined using only routine experimentation.

The term "insulin substitute" refers to any zinc containing compound which may be used in place of insulin in the supplement of the invention to give substantially similar results as insulin. Examples of insulin substitutes include but are not limited to zinc chloride, zinc nitrate, zinc bromide, and zinc sulfate.

A number of insulins are known to those of ordinary skill in the art. See Gilman, A. G. et al., Eds., *The Pharmacological Basis of Therapeutics*, Pergamon Press, New York, 1990, pp. 1463–1495. Preferably, insulin, rather than an insulin substitute, is used in the supplement and the medium of the present invention. More preferably, the insulin is zinc insulin. Most preferably, the insulin is human zinc insulin. In the supplement and the medium of the present invention, the concentration of the insulin substitute which facilitates cell growth, expansion, and differentiation in culture can be determined using only routine experimentation.

The term "expand" refers to the growth and division, and not the differentiation, of hematopoietic cells in culture. The term "differentiation" refers to the development of a cell of a particular type into a cell of another type. The development of a pluripotent hematopoietic stem cell into a myeloid precursor is an example of differentiation. Likewise, the development of precursor cell into another type of cell is an example of differentiation.

The term "antioxidant" refers to molecules which inhibit reactions that are promoted by oxygen or peroxides. Antioxidants which may be used in the supplement or the medium of the present invention include but are not limited to N-acetyl-L-cysteine or derivatives thereof (see International Patent Application WO 95/00136), 2-mercaptoethanol or derivatives thereof, D,L-tocopherol acetate or derivatives thereof, ascorbic acid or derivatives thereof, thiol compounds, such as dithiothreitol and glutathione, or derivatives of thiol compounds, catalase or derivatives thereof, cysteine or derivatives thereof, thiolactate or derivatives thereof, penicillamine or derivatives thereof, mercaptoethanesulfonic acid or derivatives thereof, and mercaptopropionic acid, or derivatives thereof. Preferably, the antioxidants used in the supplement and the medium of the present invention are N-acetyl-L-cysteine, 2-mercaptoethanol, and D,L-tocopherol acetate or mixtures or derivatives thereof.

The term "glucocorticoid" refers to steroid compounds which are in the glucocorticoid, as opposed to the mineralocorticoid, class of corticosteroids. The term includes but is not limited to glucocorticoids such as hydrocortisone, cortisol, dexamethasone, and derivatives of these compounds. See Gilman, A. G. et al., Eds., *The Pharmacological Basis of Therapeutics*, Pergamon Press, New York, 1990, pp. 1440–1462. Preferably, the glucocorticoid of the present invention is hydrocortisone.

The term "trace element" refers to a moiety which is present in a cell culture medium in only trace amounts. In the present invention, this term encompasses $Se^{4+}$, $Ag^+$, $Al^{3+}$, $Ba^{2+}$, $Cd^{2+}$, $Co^{2+}$, $Cr^+$, $Ge^{4+}$, $Se^{4+}$, $Br^-$, $I^-$, $Mn^{2+}$, $F^-$, $Si^{4+}$, $V^{5+}$, $Mo^{6+}$, $Ni^{2+}$, $Rb^+$, $Sn^{2+}$ and $Zr^{4+}$ and salts thereof. Preferably, the trace element is used in the supplement and the medium of the present invention. Any salt of a given trace element can be used to make the supplement or the medium of the present invention. For example, the sodium salt of selenium oxide (sodium selenite, $Na_2SeO_3$) is preferably used to provide selenium. Suitable concentrations of trace element-containing compounds can be determined by one of ordinary skill in the art. For example, in the medium of the invention, the concentration of $SeO_3^{2-}$ can be about 0.007 to about 0.07 mg/L. In a preferred embodiment of the medium of the invention, the concentration of $SeO_3^{2-}$ is about 0.01 mg/L.

The term "lipid agent" refers to an agent which provides a source of lipids or contributes to lipid formation. Suitable lipid agents which can be used in the supplement and the medium of the present invention include, but are not limited to, the product soluble human lipids for serum-free media, sold under the trademark HUMAN EX-CYTE®, ethanolamine (or a salt thereof), sitosterol (a plant steroid), rice hydrolysate (a mixture of proteins and lipids), LTI Defined Lipid Mixture, a mixture of arachidonic acid, cholesterol, DL-α-tocopherol-acetate, ethyl alcohol, linoleic acid, linolenic acid, myristic acid, oleic acid, palmitric acid, palmitic acid, Pluronic® F-68, stearic acid, and Tween® 80. Preferably, HUMAN EX-CYTE® (Bayer Corporation Kankakee, Ill) and ethanolamine are used in the supplement and the medium of the invention. Suitable concentrations of a lipid agent ingredient can be determined by one of ordinary skill in the art.

The term "ingredient" refers to any compound, whether of chemical or biological origin, that can be used in cell culture media to maintain or promote the growth or proliferation of cells. The terms "component," "nutrient" and "ingredient" can be used interchangeably and are all meant to refer to such compounds. Typical ingredients that are used in cell culture media include amino acids, salts, metals, sugars, lipids, nucleic acids, hormones, vitamins, fatty acids, proteins and the like. Other ingredients that promote or maintain growth of cells ex vivo can be selected by those of skill in the art, in accordance with the particular need.

By "cell culture" is meant cells or tissues that are maintained, cultured or grown in an artificial, in vitro environment.

By "culture vessel" it is meant glass containers, plastic containers, or other containers of various sizes that can provide an aseptic environment for growing cells. For example, flasks, single or multiwell plates, single or multiwell dishes, or multiwell microplates can be used. Further, a bioreactor can be used to culture cells.

The terms "cell culture medium," "culture medium" and "medium formulation" refer to a nutritive solution for culturing or growing cells.

The terms "cultivating" and "culturing" are synonymous.

The term "container means" includes culture vessels, jars, bottles, vials, straws, ampules, and cryotubes.

The term "feeding" or "fluid-changing" refers to replacing the medium in which cells are cultured.

The term "combining" refers to the mixing or admixing of ingredients in a cell culture medium formulation.

The term "contacting" refers to the mixing, adding, seeding, or stirring of one or more cells with one or more compounds, solutions, media, etc.

A "serum-free" medium is a medium that contains no serum (e.g., fetal bovine serum (FBS), horse serum, goat serum, etc.).

By "compatible ingredients" is meant those media nutrients which can be maintained in solution and form a "stable" combination. A solution containing "compatible ingredients" is said to be "stable" when the ingredients do not degrade or decompose substantially into toxic compounds, or do not degrade or decompose substantially into compounds that cannot be utilized or catabolized by the cells in culture. Ingredients are also considered "stable" if degradation can not be detected or when degradation occurs at a slower rate when compared to decomposition of the same ingredient in a 1× cell culture media formulation. Glutamine, for example, in 1× media formulations, is known to degrade into pyrolidone carboxylic acid and ammonia. Glutamine in combination with divalent cations are considered "compatible ingredients" since little or no decomposition can be detected over time. See U.S. Pat. No. 5,474,931.

A cell culture medium is composed of a number of ingredients and these ingredients vary from medium to medium. Each ingredient used in a cell culture medium has unique physical and chemical characteristics. Compatibility and stability of ingredients are determined by the "solubility" of the ingredients in solution. The terms "solubility" and "soluble" refer to the ability of an ingredient to form a solution with other ingredients. Ingredients are thus compatible if they can be maintained in solution without forming a measurable or detectable precipitate. Thus, the term "compatible ingredients" as used herein refers to the combination of particular culture media ingredients which, when mixed in solution either as concentrated or 1× formulations, are "stable" and "soluble."

A "1× formulation" is meant to refer to any aqueous solution that contains some or all ingredients found in a cell culture medium. The "1× formulation" can refer to, for example, the cell culture medium of any subgroup of ingredients for that medium. The concentration of an ingredient in a 1× solution is about the same as the concentration of that ingredient found in the cell culture formulation used for maintaining or growing cells. Briefly, a culture medium used to grow cells is, by definition, a 1× formulation. When a number of ingredients are present (as in a subgroup of compatible ingredients), each ingredient in a 1× formulation has a concentration about equal to the concentration of those ingredients in a cell culture medium. For example, RPMI 1640 culture medium contains, among other ingredients, 0.2 g/L L-arginine, 0.05 g/L L-asparagine, and 0.02 g/L L-aspartic acid. A "1× formulation" of these amino acids, which are compatible ingredients according to the present invention, contains about the same concentrations of these ingredients in solution. Thus, when referring to a "1× formulation," it is intended that each ingredient in solution has the same or about the same concentration as that found in the cell culture medium being described. The concentrations of medium ingredients in a 1× formulation are well known to those of ordinary skill in the art. See *Methods For Preparation of Media, Supplements and Substrate For Serum-Free Animal Cell Culture*, Allen R. Liss, N.Y. (1984).

A 10× formulation refers to a solution wherein each ingredient in that solution is about 10 times more concentrated than the same ingredient in the cell culture media. RPMI 1640 media, for example, contains, among other things, 0.3 g/L L-glutamine. A "10× formulation" may contain a number of additional ingredients at a concentration about 10 times that found in the 1× culture media. As will be apparent, "25× formulation," "50× formulation," and "100× formulation" designate solutions that contain ingredients at about 25, 50 or 100 fold concentrations, respectively, as compared to a 1× cell culture media.

The term "inorganic salt" refers to a salt of $Ca^{2+}$, $K^+$, $Mg^{2-}$, $Na^+$, $CO_3^{2-}$, $PO_4^{3-}$. Any salt of each of these moieties can be used to make the medium of the present invention. For example, the following salts can be used: $CaCl_2$, KCL, $KNO_3$, $MgSO_4$, NaCl, $NaHCO_3$, and $NaH_2PO_4$-water.

Examples of concentrations of compounds containing $Ca^{2+}$, $K^+$, $Mg^{2+}$, $Na^+$, $CO_3^{2-}$, and $PO_4^{3-}$ are as follows. In the 1× medium of the present invention, the concentration of $Ca^{2+}$ is about 0.3 to about 140 mg/L, the concentration of $K^+$ is about 0.5 to about 250 mg/L, the concentration of $Mg^{2+}$ is about 10 to about 100 mg/L, the concentration of $Na^+$ is about 1200 to about 3700 mg/L, the concentration of $CO_3^{2-}$ is about 70 to about 2900 mg/L, and the concentration of $PO_4^{3-}$ is about 7 to about 500 mg/L. In a preferred embodiment, the concentration of $Ca^{2+}$ is about 45 mg/L, the concentration of $K+$ is about 170 mg/L, the concentration of $Mg^{2+}$ is about 20 mg/L, the concentration of $Na^+$ is about 1900 mg/L, the concentration of $CO_3^{2-}$ is about 2100 mg/L, and the concentration of $PO_4^{3-}$ is about 90 mg/L.

The term "energy source" refers to a carbohydrate source. Suitable energy sources which can be used in the supplement and the medium of the present invention include D-fructose, D-mannose, and D-galactose. Preferably, the energy source used is D-glucose.

The term "buffering agent" refers to an agent which acts to stabilize the hydrogen ion concentration and therefore the pH of a solution by neutralizing, within limits, both acids and bases. Suitable buffering agents which can be used in the supplement and the medium of the present invention include N-[2-hydroxyethyl]piperazine-N'-[2-ethanesulfonic acid] (HEPES), β-glycerol-phosphate, and bicarbonate buffer. Preferably, in the supplement and the medium of the present invention, HEPES is used.

The term "amino acid" refers to amino acids or their derivatives (e.g., amino acid analogs), as well as their D- and L-forms. Examples of such amino acids include glycine, L-alanine, L-asparagine, L-cysteine, L-aspartic acid, L-glutamic acid, L-phenylalanine, L-histidine, L-isoleucine, L-lysine, L-leucine, L-glutamine, L-arginine, L-methionine, L-proline, L-hydroxyproline, L-serine, L-threonine, L-tryptophan, L-tyrosine, and L-valine.

"$CD34^+$ hematopoietic cells" or "$CD34^+$ cells" are hematopoietic cells which express the $CD34^+$ surface marker protein. Such cells include but are not limited to hematopoietic stem cells, myeloid progenitor or precursor cells, erythroid progenitor or precursor cells, and lymphoid progenitor or precursor cells.

A preparation of cells enriched for $CD34^+$ cells can be obtained from bone marrow, peripheral blood and neonatal cord blood using methods that are well known by those of ordinary skill in the art. Various systems are available to those of ordinary skill in art. For example, the MicroCELLector System® (Applied Immune Sciences), the MiniMacs System (Miltenvi Biotec), the StemSep™ system (StemCell Technologies) can be used can be used to isolate $CD34^+$ cells. To prepare a preparation of cells enriched for $CD34^+$ cells on a larger scale, systems marketed by Baxter Healthcare and CellPro are available to those of ordinary skill in the art.

The terms "hematopoietic stem cell" and "pluripotent hematopoietic stem cell" refer to a cell which can give rise to any type of hematopoietic progenitor or precursor cell, including myeloid progenitor or precursor cells, erythroid progenitor or precursor cells, and lymphoid progenitor or precursor cells. Hematopoietic stem cells display a $CD34^+/CD33^-/CD38^-$ phenotype or a $CD34^+/HLD-DR^-/CD38^-$ phenotype (Daley, J. P. et al., *Focus* 18:62–67 (1996); Pimentel, E., Ed., *Handbook of Growth Factors Vol. III: Hematopoietic Growth Factors and Cytokines*, pp. 1–2, CRC Press, Boca Raton, Fla., 1994).

A "population" of cells refers to any number of cells greater than one.

The terms "recombinant CD34+ hematopoietic cell" refers to a CD34+ hematopoietic cell into which a nucleic acid molecule has been introduced and has become stably maintained. The nucleic acid molecule can contain a drug resistance gene which aids in the selection of recombinant CD34+ hematopoietic cells. After introduction of the nucleic acid molecule and clonal drug selection, ES clones are analyzed by either PCR or Southern blotting methods to verify correct gene targeting.

The term "nucleic acid construct" refers to a nucleic acid molecule which contains a sequence which encodes a protein of interest. Preferably, the nucleic acid construct is an expression vector which contains the nucleic acid encoding the protein of interest operably linked to an expression control sequence (i.e., a promoter and/or an enhancer, regulatory sequences to which gene regulatory proteins bind and exert control over gene transcription). Expression vectors which may be used are well known to those of ordinary skill in the art.

The term "basal medium" refers to any medium which is capable of supporting growth of CD34+ hematopoietic cells, or other cells, when supplemented either with serum or with the serum-free supplement of the present invention. The basal medium supplies standard inorganic salts, such as zinc, iron, magnesium, calcium and potassium, as well as trace elements, vitamins, an energy source, a buffer system, and essential amino acids. Basal media which can be used in the present invention include but are not limited to Iscove's Modififed Dulbecco's Medium, RPMI 1640, Minimal Essential Medium-α (MEM-α), and other media disclosed infra. In a preferred embodiment, the basal medium is Iscove's Modififed Dulbecco's Medium.

The terms "serum-free culture conditions" and "serum-free conditions" refer to cell culture conditions that exclude serum of any type.

The present invention provides a serum-free, eukaryotic cell culture medium supplement comprising one or more ingredients selected from the group consisting of one or more antioxidants, one or more albumins or albumin substitutes, one or more lipid agents, one or more insulins or insulin substitutes, one or more transferrins or transferrin substitutes, one or more trace elements, and one or more glucocorticoids, wherein a basal cell culture medium supplemented with the supplement is capable of supporting the expansion of CD34+ hematopoietic cells in serum-free culture.

The present invention also specifically provides a serum-free, eukaryotic cell culture medium supplement comprising one or more ingredients selected from the group consisting of N-acetyl-L cysteine, human serum albumin, HUMAN EX-CYTE®, ethanolamine HCl, human zinc insulin, human iron saturated transferrin, $Se^{4+}$, hydrocortisone, D,L-tocopherol acetate, and 2-mercaptoethanol.

The concentration ranges within which ingredients are believed to support the growth of CD34+ hematopoietic cells are listed in Tables 1–3. These ingredients can be combined to form the cell culture medium supplement of the present invention. As will be readily apparent to one of ordinary skill in the art, the concentration of a given ingredient can be increased or decreased beyond the range disclosed and the effect of the increased or decreased concentration can be determined using only routine experimentation.

The supplement of the present invention is the StemPro-34™ Nutrient Supplement. The quantitative description of this formulation, including final concentrations of the ingredients, is shown in Table 1. The supplement of the present invention can be concentrated (infra). Preferably, the supplement of the present invention is about a 40x formulation (See Table 2). In a preferred embodiment, of the present invention, the concentrated nutrient supplement is admixed with a 1x basal medium (e.g., Iscove's Modified Dulbecco's Medium).

To make a 40x formulation of the Stempro-34™ Nutrient supplement, the product soluble human lipids for serum-free media, sold under the trademark HUMAN EX-CYTE®, is added in dropwise fashion to 25% human albumin. To this mixture is added ethanolamine HCl, followed by sodium selenite, hydrocortisone, and D,L-tocopherol acetate. Insulin is then solubilized in 0.05 M HCl. The pH of the insulin solution is then adjusted to 9.0 and is added to the mixture. Next, human transferrin is added, followed by 2-mercaptoethanol.

N-acetyl-L-cysteine is solubilized in double-distilled water. The pH of the N-acetyl-L-cysteine at this point is approximately 2.0. To prevent protein denaturation, the pH of the N-acetyl-L-cysteine is adjusted to 7.0 with 5N sodium hydroxide and is added to the mixture. The entire mixture is then filtered through a 0.2 micron low protein binding filter.

The medium of the present invention is StemPro™-34 serum-free medium (SFM). The quantitative description of this formulation, including final concentrations of the ingredients after addition to a basal medium to form a 1x formulation, is shown in Table 3.

Preferably, the supplement of the present invention is stored at about 4° C. and most preferably at about −20° C., although the supplement may be stored at lower temperatures (e.g., about −80° C.). Preferably, the medium of the present invention is stored at about 4° C. When the medium of the present invention includes the ingredient N-acetyl-L-cysteine, the medium was stable after having been stored for greater than eighteen months at 4° C. Thus, even after greater than eighteen months of storage, the medium of the present invention supports the expansion of CD34+ hematopoietic cells.

As will be apparent to one of ordinary skill in the art, the ingredients may react in solution. Thus, the present invention encompasses the formulations disclosed in any of Tables 1–3 as well as any reaction mixture which forms after the ingredients in any one of Tables 1–3 are combined.

The concentrations of the supplement ingredients in Table 3 are obtained when 24.8 mL of the 40x supplement formulation (Table 2) are diluted in one liter of basal medium. Alternatively, the concentrations of supplement ingredients shown in Table 3 can be obtained by making the medium of the present invention as a complete formulation (rather by than adding the supplement to a basal medium).

The supplement or the medium of the present invention can be in liquid form or can be maintained in dry form. The type of liquid carrier and the method used to dissolve the ingredients into solution vary and can be determined by one of ordinary skill in the art with no more than routine experimentation. In general, the liquid carrier is water.

The supplement or the medium of the present invention can be made as a concentrated formulation (greater than 1x to 1000x) or as a 1x formulation. Preferably, the solutions comprising ingredients are more concentrated than the concentration of the same ingredients in a 1x media formulation. For example, the ingredients can be 10 fold more concentrated (10x formulation), fold more concentrated (25x formulation), 50 fold more concentrated (50x concentration), or 100 fold more concentrated (100× formulation). In particular, the supplement or the medium of the present invention can be made by dividing the ingredients into compatible, concentrated subgroups. See U.S. Pat. No. 5,474,931.

If the ingredients of the supplement or the medium are prepared as separate concentrated solutions, an appropriate (sufficient) amount of each concentrate is combined with a diluent to produce a less concentrated formulation or a 1× formulation. Typically, the diluent for the subgroups used is water but other solutions including aqueous buffers, aqueous saline solution, or other aqueous solutions may be used according to the invention.

TABLE 1

StemPro ™-34 Nutrient Supplement Formulation

| Ingredient | Concentration Range in 1X Medium (mg/L) (About) | A Preferred Embodiment (mg/L) (About) |
|---|---|---|
| Human Serum Albumin | 1000–15,000 | 5000 |
| HUMAN EX-CYTE ® | 1–15 | 5.0 |
| Ethanolamine | 1–25 | 10 |
| Sodium Selenite | 0.0001–0.01 | 0.005 |
| Hydrocortisone | 0.003–0.07 | 0.04 |
| D,L-Tocopherol | 0.005–0.05 | 0.02 |
| Iron Saturated Human Transferrin | 10–500 | 100 |
| Human Zinc Insulin | 1–25 | 10 |
| N-acetyl-L-cysteine | 16–660 | 160 |
| 2-Mercaptoethanol | 2–8 | 4 |

TABLE 2

StemPro ™ -34 Nutrient Supplement Formulation (40X)

| Ingredient | Concentration (mg/L) (About) |
|---|---|
| Human Serum Albumin | 200,000 |
| HUMAN EX-CYTE ® | 200 |
| Ethanolamine · HCl | 400 |
| Sodium Selenite | 0.2 |
| Hydrocortisone | 2 |
| D,L-Tocopherol | 0.8 |
| Iron Saturated Human Transferrin | 4 |
| Human Zinc Insulin | 400 |
| N-acetyl-L-cysteine | 7 |
| 2-Mercaptoethanol | 180 |

TABLE 3

StemPro ™-34 SFM Medium Formulation

| Ingredient | Concentration Range in 1X Medium (mg/L) (About) | A Preferred Embodiment (mg/L) (About) |
|---|---|---|
| Inorganic Salts | | |
| $CaCl_2$ | 1–500 | 165 |
| KCL | 1–500 | 330 |
| $KNO_3$ | 0.008–0.8 | 0.08 |
| $MgSO_4$ | 10–500 | 100 |
| NaCl | 3000–9000 | 4500 |
| $NaHCO_3$ | 100–4000 | 3000 |
| $NaH_2PO_4$ · water | 10–750 | 125 |

TABLE 3-continued

StemPro ™-34 SFM Medium Formulation

| Ingredient | Concentration Range in 1X Medium (mg/L) (About) | A Preferred Embodiment (mg/L) (About) |
|---|---|---|
| Amino Acids | | |
| L-Alanine | 5–250 | 25 |
| L-Asparagine (free base) | 5–150 | 25 |
| L-Arginine HCl | 10–250 | 84 |
| L-Aspartic Acid | 5–125 | 30 |
| L-Cystine 2 · HC1 | 1–200 | 90 |
| L-Glutamic Acid | 5–500 | 75 |
| Glycine | 5–200 | 30 |
| L-Histidine · HCl · water | 5–200 | 42 |
| L-Isoleucine | 5–500 | 105 |
| L-Leucine | 25-500 | 105 |
| L-Methionine | 5–500 | 30 |
| L-Phenylalanine | 5–500 | 70 |
| L-Proline | 5–500 | 40 |
| L-Serine | 5–500 | 40 |
| L-Threonine | 5–500 | 100 |
| L-Lysine · HCl | 25–500 | 150 |
| L-Tryptophan | 2–100 | 15 |
| L-Tyrosine (disodium salt) | 25–500 | 100 |
| L-Valine | 5–500 | 95 |
| Vitamins | | |
| Biotin | 0.01–1.0 | 0.01 |
| D-Ca Pantothentate | 0.05–10.0 | 4 |
| Choline Chloride | 1–150 | 4 |
| Folic Acid | 0.1–10.0 | 4.00 |
| i-Inositol | 1–75 | 7 |
| Niacinamide | 0.1–10.0 | 4 |
| Pyridoxal · HCl | 0.1–10.0 | 4 |
| Riboflavin | 0.01–2.0 | 0.4 |
| Thiamine · HCl | 0.1–10.0 | 4 |
| Vitamin $B_{12}$ | 0.001–5.0 | 0.001 |
| Other Components | | |
| Human Serum Albumin | 1000–15,000 | 5000 |
| $Na_2SeO_3$ | 0.001–0.01 | 0.02 |
| D-Glucose | 2000–9000 | 4500 |
| Phenol Red | 0.5–30 | 15 |
| HEPES | 1000–7000 | 6000 |
| Sodium Pyruvate | 10–300 | 110 |
| HUMAN EX-CYTE ® | 1–15 | 5 |
| Ethanolamine | 1–25 | 10 |
| Hydrocortisone | 0.003–0.07 | 0.04 |
| D,L-Tocopherol | 0.005–0.05 | 0.02 |
| Iron Saturated Human Transferrin | 10–500 | 100 |
| Human Zinc Insulin | 1–25 | 10 |
| N-acetyl-L-cysteine | 16–660 | 160 |
| 2-Mercaptoethanol | 2–8 | 4 |

The supplement or the medium or concentrated formulation of the present invention (both aqueous and dry forms) are typically sterilized to prevent unwanted contamination. Sterilization may be accomplished, for example, by ultra-violet light, filtration, or heat.

All of the ingredients of the supplement of the present invention which are of human origin (e.g., human serum albumin, transferrin, and HUMAN EX-CYTE®) are heat treated, prior to use, by heating at 60° C. for 10 hours.

The osmolarity of the 40× supplement of the present invention can be in the range of about 200 to about 400 mOsm, and is preferably from about 250 to about 350 mOsm. The pH of the 40× supplement can be in the range from about 6 to about 8, is preferably from about 6.4 to about 7.4. The osmolarity of the medium of the present invention can be in the range from about 200 to about 400, and is preferably from about 270 to about 310 mOsm. The pH of the medium of the present invention can be in the range from about 6 to about 8, and is preferably from about 6.8 to about 7.3.

Those of ordinary skill in the art are familiar with methods for culturing hematopoietic cells. For example, guidelines for hematopoietic cell culture are outlined in Freshney, R. I. et al., Eds., *Culture of Hematopoietic Cells*, Wiley-Liss, New York, 1994, pp. 81–98.

The present invention also provides a kit comprising a carrier means such as a box or carton being compartmentalized to receive in close confinement therein one or more container means such as vials, tubes, ampules, jars, and the like, wherein a first container means contains the supplement of the present invention. Optionally, a second container means contains a basal medium. Preferably, the container containing the supplement of the present invention can be stored from about −135 to about 4° C., preferably from about −5 to about −80° C., most preferably from about −5 to about −20° C., and still more preferably at about −20° C. A container containing the medium of the invention is preferably stored at about 2 to about 8° C., and most preferably at about 4° C.

The present invention also provides a composition comprising $CD34^+$ hematopoietic cells in a serum-free medium, wherein the serum-free medium, which is supplemented with the serum-free supplement of the invention, is capable of supporting the growth of the $CD34^+$ hematopoietic cells in serum-free culture. Aliquots of this composition can be frozen at about −80° C. and below. Aliquots of this composition can be stored indefinitely at less than or equal to about −135° C. After an aliquot of the composition has been thawed and opened, using sterile cell culture technique, the $CD34^+$ hematopoietic cells can be cultivated in serum-free culture. Animals from which $CD34^+$ or equivalent hematopoietic cells can be obtained include human, monkey, ape, mouse, rat, hamster, rabbit, guinea pig, cow, swine, dog, horse, cat, goat, and sheep. Equivalent hematopoietic cells are cells from non-human species which are regarded by those of ordinary skill in the art as hematopoietic stem cells, based on the expression of surface marker proteins.

It is also routine to freeze hematopoietic cells for use at a later date. Freezing media generally consist of 5–10% DMSO, 10–90% FBS and 55–85% eukaryotic cell culture media. The supplement of the present invention can be used as a serum substitute for cryopreservation and reconstitution purposes. The conditions for cryopreservation of such cells with the supplement of the invention include 0.5–95% supplement, 1–10% of a cryoprotectant (e.g., dimethylsulfoxide (DMSO)), and 1–90% of a basal medium. $CD34^+$ hematopoietic cells can be frozen under such conditions at about −80° C. and below. $CD34^+$ hematopoietic cells can remain frozen indefinitely at temperatures less than or equal to about −135° C.

The medium of the present invention can be supplemented with growth factors or other cytokines in order to facilitate the expansion and/or the differentiation of $CD34^+$ hematopoietic cells. $CD34^+$ hematopoietic cells can be incubated with specific factors in order to facilitate expansion or to induce differentiation of the $CD34^+$ hematopoietic cells into a particular type of cell. Such factors are well know to those of ordinary skill in the art. Such factors include, but are not limited to, interleukins, cytokines, colony stimulating factors, growth factors, and interferons. Examples of such factors include but are not limited to stem cell factor, an interleukin (IL) such as IL-1, IL-2, IL-3, IL-4, IL-5, IL-6, IL-7, IL-8, IL-9, IL-10, IL-11, IL-12, CSF, G-CSF, thrombopoietin (TPO), GM-CSF, erythropoietin (EPO), Flt3, Flt2, PIXY 321, and leukemia inhibitory factor (LIF). Such factors can be used to expand $CD34^+$ stem cells or as differentiation factors to cause stem cells to differentiate into a different cell type.

The present invention also provides a method of providing $CD34^+$ hematopoietic cells to a mammal, the method comprising contacting $CD34^+$ hematopoietic cells with the medium of the present invention, cultivating cells under conditions suitable to facilitate the expansion of the cells in serum-free culture, and introducing the expanded cells into a mammal.

The serum-free supplement of the present invention can also be used to prepare a hematopoietic cell type of interest for explantation into a mammal. In this embodiment, cells which have been caused to differentiate (supra) are introduced into a mammal. For example, $CD34^+$ hematopoietic cells which have been caused to differentiate into a hematopoietic stem, precursor, or progenitor cell can be introduced into the bone marrow or the bloodstream of the mammal. The $CD34^+$ or differentiated cells can be introduced into, for example, the bone marrow or bloodstream of the mammal by well-known techniques.

Having now fully described the present invention, the same will be more clearly understood by reference to certain specific examples which are included herewith for purposes of illustration only, and are not intended to be limiting of the invention.

EXAMPLE 1

Experimental Methods

In the examples that follow, unless otherwise indicated, the methods of obtaining bone marrow cells, selecting $CD34^+$ cells, assaying cell proliferation, and flow cytometry assays were performed as described in this Example.

Bone Marrow Cells

Bone marrow was obtained from a population of screened normal donors (courtesy of Roswell Park Cancer Institute). Marrow was aspirated from the posterior iliac crest and placed into sterile heparinized tubes. In the laboratory, approximately 25 mL of heparinized bone marrow was diluted with an equal volume of Hank's Balanced Salt Solution (without calcium or magnesium) (Life Technologies, Gaithersburg, MD) and carefully layered over Nycoprep™ 1.077 (Life Technologies) in 50 mL tubes. Samples were then centrifuged at 800×g for 30 minutes at room temperature. After centrifugation, the band of bone marrow mononuclear cells (BMMC) at the interface was removed by pipetting. Cells were washed once with Hank's Balanced Salt Solution (without calcium or magnesium) and counted using a hemocytometer (using trypan blue dye exclusion to measure cell viability).

$CD34^+$ Cell Selection

For some experiments, $CD34^+$ cells were separated using the MicroCELLector® System according to the manufacturer's instructions. Briefly, the non-adherent fraction of BMMC was collected after incubation on Soybean Agglutinin MicroCELLector® flasks. Cells were washed with Iscove's Modified Dulbecco's Medium (IMDM).

For some experiments, $CD34^+$ cells were separated using the MiniMACS system according to the manufcturer's instructions. Briefly, mononucleated cells were suspended at a concentration of $10^8$ cells in 300 µl of buffer (PBS/0.5% human serum albumin/ACD solution 1:10). Blocking reagent and antibody reagent from the CD34 Isolation Kit were added simultaneously to the suspension. The suspension was mixed well and allowed to incubated at 6 to 12° C. for fifteen minutes. After incubation, the cells were washed in buffer by centrifugation at 1200 RPM for ten minutes. The supernatant was removed and the cell pellet was resuspended in 400 µl of buffer. The colloidal syspenesion of submicroscopic magnetic beads was added to the cells. Cells were mixed and incubated at 6 to 12° C. for fifteen minutes. Cells were again wahsed by centrigugation, the supernatant was removed, and the cells were resuspended in 500 µl of buffer. Separation columns were prepared by rinsing with 2 mL of buffer and placed in a magnetic field. Cells were applied to the column and eluted by gravity. CD34$^+$ cells were retained on the column. The column was rinsed with 2 mL of buffer. CD34$^+$ cells were eluted by removing the column from the magnetic field nad flushing the column with 2 mL of buffer.

CD34$^+$ Cell Culture

For a given experiment, the CD34$^+$ cells that were used were cells that had been isolated by only one of the above methods. Unless indicated otherwise, CD34$^+$ cells were incubated at 37° C. in 5% CO$_2$/95% air atmosphere. Cells were counted using a hemocytometer. Cell viability was assessed by the ability of the cells to exclude trypan blue dye.

Cell Proliferation Assay

CD34$^+$ cells were cultured for 6 to 8 days in either StemPro-34™ SFM (Life Technologies) supplemented with recombinant growth factors or IMDM supplemented with 20% fetal bovine serum and recombinant growth factors. Unless otherwise indicated, recombinant growth factors were added at the beginning of the setup of a cell culture experiment.

Cells were seeded at an initial density of 2×10$^4$ cells/mL (1×10$^4$ cells/cm$^2$) in 24-well culture plates without additional feeding. At the end of the incubation period, cells were harvested and cell expansion was determined by hemocytometer counting. Aliquots of harvested cells were removed for further analysis in colony forming unit assays and phenotypic analysis by fluorescence activated cell sorting.

Flow Cytometry

Freshly selected or cultured cell populations were stained with fluorochrome-labeled monoclonal antibodies as follows. Aliquots of cells were incubated on ice for 15 minutes with mouse IgG to block nonspecific binding sites. The cells were then added to 12×75 mm polystyrene tubes containing either the FITC- or PE-conjugated monoclonal antibodies. These tubes were mixed and incubated on ice for 30 to 45 minutes. The stained cells were then washed one time with Dulbecco's Phosphate Buffered Saline (DPBS) and fixed with 2% formalin/DPBS. Analysis was carried out using a FACSort apparatus (Becton Dickinson (BD)). The standard panel of fluorochrome-conjugated antibodies was anti-CD34/HPCA-2 (BD), anti-CD14/MøP9 (BD), anti-CD38/T16 (Immunotech, Inc.), anti-CD13/366 (Coulter Corp.), and anti-CD33/906 (Coulter).

EXAMPLE 2

Proliferation of CD34$^+$-Selected Cells Under Serum-Free Culture Conditions In order to study the ability of CD34$^+$ cells to expand and differentiate under various culture conditions, CD34$^+$ cells were selected from normal donor bone marrow. Initially, 1.3% of the total bone marrow cells were CD34$^+$ (Table 4), in agreement with reported values (Cinin, C. I. et al., *J. Immunol.* 133:157 (1984)). The selection process enriched CD34$^+$ cells to 64% from 1% in freshly aspirated normal bone marrow cells.

The absence of serum allows the study of the effect of early-acting or late-acting hematopoietic growth factors on cell expansion. Various combinations of human recombinant cytokines were examined for their ability to support proliferation (Table 5). Using StemPro-34™ SFM, it was possible to stimulate variable degrees of cell proliferation, in the absence of the confounding effects of serum, by altering the combinations of growth factors employed.

In preliminary studies, stem cell factor alone did not affect expansion under serum-free conditions (data not shown). The addition of combinations of early-acting (e.g., SCF, IL-1, IL-3) and mid-acting (e.g., IL-6) pleiotropic cytokines had marginal growth-promoting effects under serum-free conditions (Table 5). The stimulation of cell expansion required a combination of early-(SCF, IL-3), mid- (IL-6) and late- (GM-CSF, EPO) acting differentiation factors that play a role in hematopoiesis.

TABLE 4

CD34$^+$ Population Characteristics of Bone Marrow Aspirates From Normal Donors

| Donors Evaluated | Total BMMC (× 10$^6$) | Total selected CD34* (× 10$^5$) | % Total BMMC | % Purity of Selected CD34$^+$ cells |
|---|---|---|---|---|
| MicroCELLector ® System | | | | |
| 22 | 101 ± 12 | 12 ± 2 | 1.3 ± 0.1 | 64 ± 2 |
| MiniMACS System | | | | |
| 24 | 61 ± 5 | 18.3 ± 2.3 | 2.9 ± 0.3 | 44 ± 4 |

Data are the mean ± S.E.M.
% purity of selected CD34$^+$ cells was determined by FACS analysis.

The expansion index in StemPro-34™ SFM, with various cytokines, was compared to that of cells cultured in IMDM supplemented with 20% FBS, SCF, IL-3, and GM-CSF (Table 5). This growth factor cocktail (SCF, IL-3, and GM-CSF) is commonly used when culturing hematopoietic cells in serum-supplemented medium (Haycock, D. N. et al., *Blood* 80:1405 (1992)).

TABLE 5

Cytokine-Driven Proliferation of Selected CD34$^+$ Cells in StemPro-34 $^{SM}$ SFM Medium

| SCF (100 ng/mL) | IL-1 (10 ng/mL) | IL-3 (50 ng/mL) | IL-6 (10 ng/mL) | GM-SCF (25 ng/mL) | EPO (6 ng/mL) | Expansion Index[1] | % FBS[2] |
|---|---|---|---|---|---|---|---|
| + | − | + | − | + | − | 24 | 100 |
| + | + | − | − | − | − | 5 | 19 |
| + | − | − | + | − | − | 5 | 19 |
| + | − | + | − | − | − | 7 | 27 |
| + | − | − | − | + | − | 12 | 51 |
| + | − | − | − | − | + | 19 | 76 |
| + | + | − | − | − | + | 22 | 90 |
| + | − | + | − | − | + | 29 | 120 |

TABLE 5-continued

Cytokine-Driven Proliferation of Selected CD34+ Cells in StemPro-34 SM SFM Medium

| SCF (100 ng/mL) | IL-1 (10 ng/mL) | IL-3 (50 ng/mL) | IL-6 (10 ng/mL) | GM-SCF (25 ng/mL) | EPO (6 ng/mL) | Expansion Index[1] | % FBS[2] |
|---|---|---|---|---|---|---|---|
| + | − | − | − | + | + | 30 | 122 |
| + | + | + | + | + | − | 42 | 171 |

Data are a representative study.
[1] The expansion index indicates the level of amplification of the cell population as determined by the equation: Cells at day $7 \div 2 \times 10^4$.
[2] % FBS = experimental group cells at day 7 ÷ cells in FBS control group at day 7 × 100% (FBS control is cells cultured in IMDM + 20% FBS + SCF + IL-3 + GM-CSF).

EXAMPLE 3

Kinetics of CD34+ Cell Expansion

The kinetics of cell expansion in StemPro-34™ SFM were compared to the kinetics of cell expansion in serum-containing medium. CD34+ bone marrow cells were seeded at an initial density of $2 \times 10^4$ cells/well in 24 well plates. Final concentrations of human recombinant factors SCF (100 ng/mL), IL-3 (50 ng/mL) and GM-CSF (25 ng/mL) were added to either StemPro™-34 SFM or IMDM/20% FBS at setup. On the days indicated, wells were harvested and the cells counted using a hemocytometer and trypan blue dye exclusion. Results are depicted in FIG. 1.

In both StemPro-34™ SFM and the serum-supplemented cultures, an initial lag phase (about 3 days) was observed to precede cell expansion. This initial lag phase may reflect experimental observations that the majority of hematopoietic stem cells (i.e., CD34+/CD33−/CD38−) are in a quiescent $G_0$ state and require stimulatory signals for expansion and subsequent differentiation (Traycoff, C. M. et al., *Exp. Hematol.* 22:1264 (1994)). After 10 days, there were about three times as many cells in StemPro-34™ SFM, compared to the serum-supplemented culture.

Cell-doubling times were calculated from the regression lines of the exponential growth phase of the curves in FIG. 1. In StemPro-34™ SFM, cells displayed a doubling time of 43 hours. In the serum-supplemented medium, doubling time was 72 hours. These doubling times reflect the total population kinetics. The cell population is heterogeneous during exponential growth as cells are not only growing but are also responding to differentiation signals.

One of ordinary skill in the art will readily understand that the supplement or the medium of the present invention, in combination with suitable growth factors, facilitates the expansion of hematopoietic progenitor cells (i.e., CD34+ cells) to levels approximately 3.5-fold above those obtained when the same combination of growth factors is added to medium supplemented with serum. Thus, one can measure the true proliferative response to combination of recombinant cytokines in the absence of the apparent and undefined components present in serum.

EXAMPLE 4

Expansion of CD34+ Cells

Changes in the CD34+ cell population during cell expansion were examined. CD34+ bone marrow cells were seeded at $2 \times 10^4$ cells per mL in 24 well flat bottomed plates and culture for 6 to 8 days in either StemPro™-34 SFM for IMDM+20% FBS. All cultures were supplemented with final concentrations of the human recombinant growth factors SCF (100 ng/mL), IL-3 (50 ng/mL) and GM-CSF (25 ng/mL) at the time of setup. Total cell counts were determined by hemocytometer and trypan blue dye exclusion. CD34+ cells were enumerated by FACS.

Figure 2:
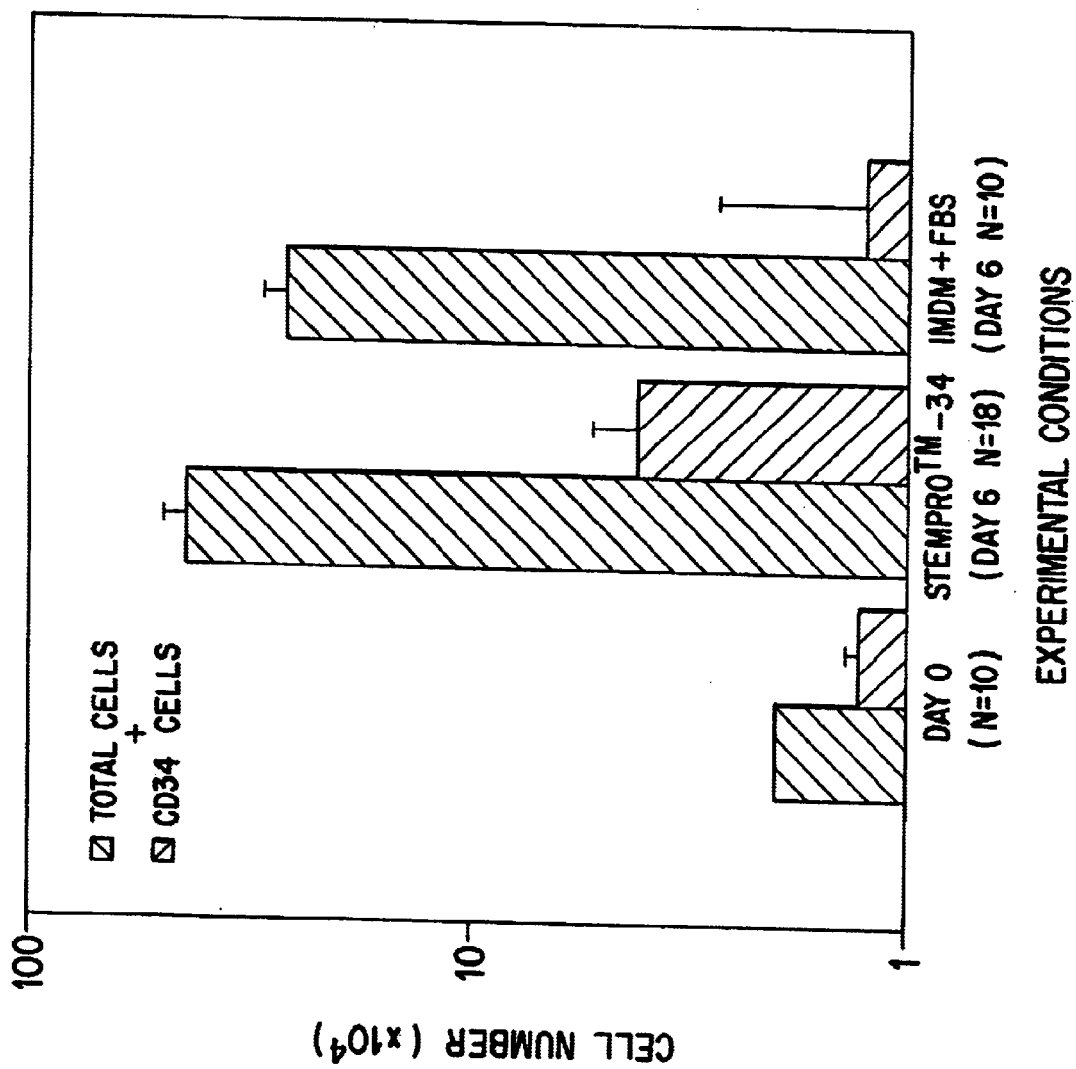
FIG. 2 shows the effect of the serum-free StemPro-34™ medium on the preferential expansion of CD34+ cells from an enriched population of CD34+ cells, as compared to the effect of serum.

As shown in FIG. 2, in StemPro-34™ SFM, the CD34+ population of cells increased 3-fold and the total population of cells increase about 22-fold. In contrast, in serum-supplemented medium, the CD34+ population of cells actually declined by 3%, while the total cell population increased about 13-fold. Thus, the supplement and the medium of the present invention support the expansion of CD34+ cells in culture. These results are the first, to date, which demonstrate an expansion of CD34+ cells in culture.

The CD34+ cell population in StemPro-34™ SFM was analyzed for several cell surface markers (Table 6). The cocktail of cytokines used stimulated the expansion of myeloid cells, as demonstrated by the increase in CD13 antigen, a protein expressed by early myeloid precursor cells.

TABLE 6

CD Antigen Expression On Hematopoietic Progenitor Cells

| Antigen | Day 0[1] | Day 6–8[1] StemPro-34 ™ SFM | IMDM +20% FBS |
|---|---|---|---|
| CD34 | 64.4 ± 4.8 | 10.8 ± 2.6 | 14.9 ± 4.1 |
| CD14 | 0.5 ± 0.2 | 1.9 ± 0.5 | 8.4 ± 1.7 |
| CD33 | 12.5 ± 4.5 | 16.9 ± 7.6 | 27.2 ± 11.5 |
| CD38 | 67.8 ± 4.1 | 34.8 ± 2.4 | 58.4 ± 4.8 |
| CD13 | 40.0 ± 7.1 | 77.3 ± 3.6 | 73.7 ± 4.8 |

[1] Data are percent positive cells. Data are expressed as mean ± S.E.M. for N = 10.

The morphological characteristics of CD34+ cells present after 6 days of growth in StemPro-34™ SFM reflect the myeloid nature of the cells. The cytoplasm of Wright-Giemsa stained cells displayed an intensely basophilic character, a large nuclear-to-cytoplasmic ratio, a delicate chromatin pattern, and clearly visible nucleoli (Daley, J. P. et al., *Focus* 18:62–67 (1996)).

EXAMPLE 5

Effect of Growth Factor Addition on Expansion

Figure 3:
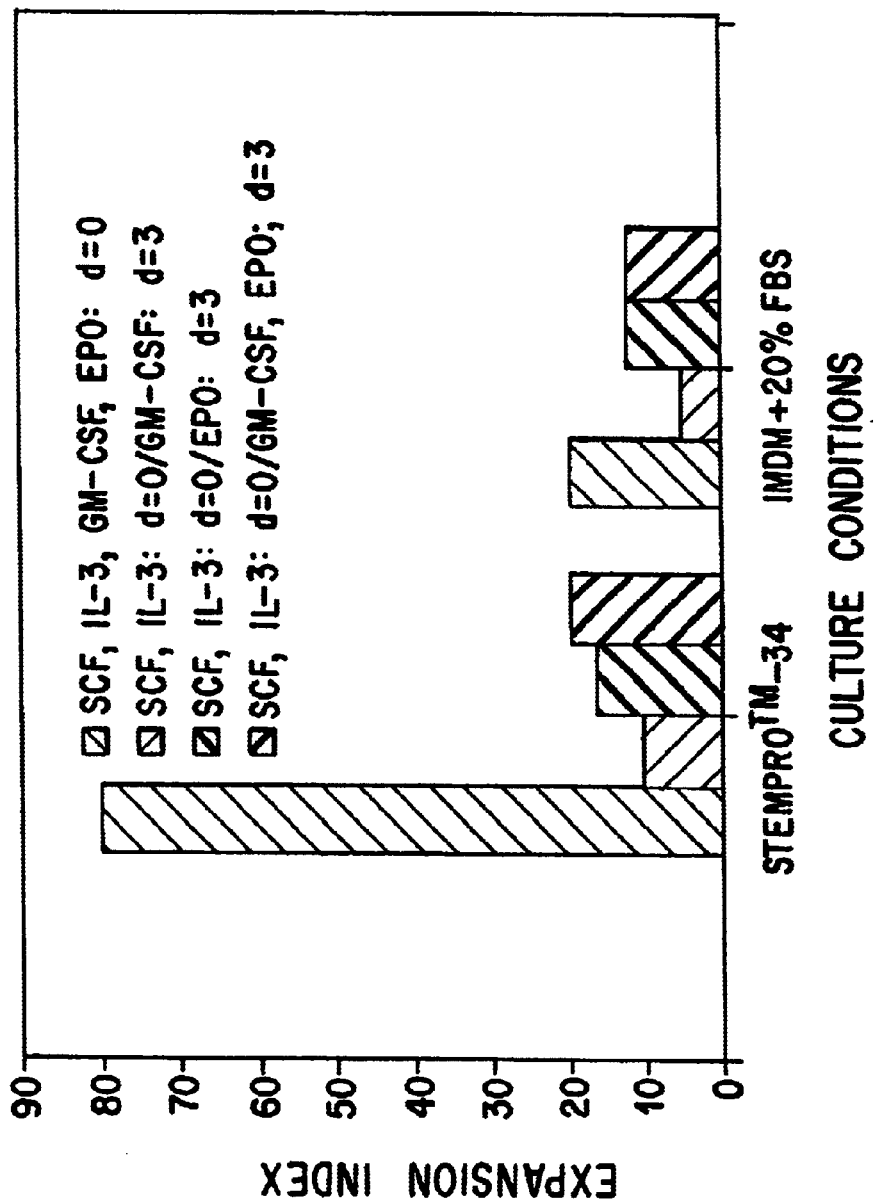
FIG. 3 shows the effect of the serum-free StemPro-34™ medium on expansion index of bone marrow cells, as compared to the effect of serum.

The advantageous effect of the supplement and the medium of the present invention is further depicted in FIG. 3. CD34+ selected cells from normal bone marrow were plated at a density of $2 \times 10^4$ cells per mL in StemPro™-34. Human recombinant growth factors were added to final concentrations of 100 ng/mL SCF 50 ng/mL IL-3, and 25 ng/mL GM-CSF the day (d) indicated and the cells were incubated for 7 days. The expansion index was calculated as (day 7 cell density÷ initial seeding density). The expansion index was about 4-fold in StemPro-34™, as compared to IMDM supplemented with 20% FBS.

EXAMPLE 6

Effect of Growth Factor Addition on Expansion

Figure 4A:
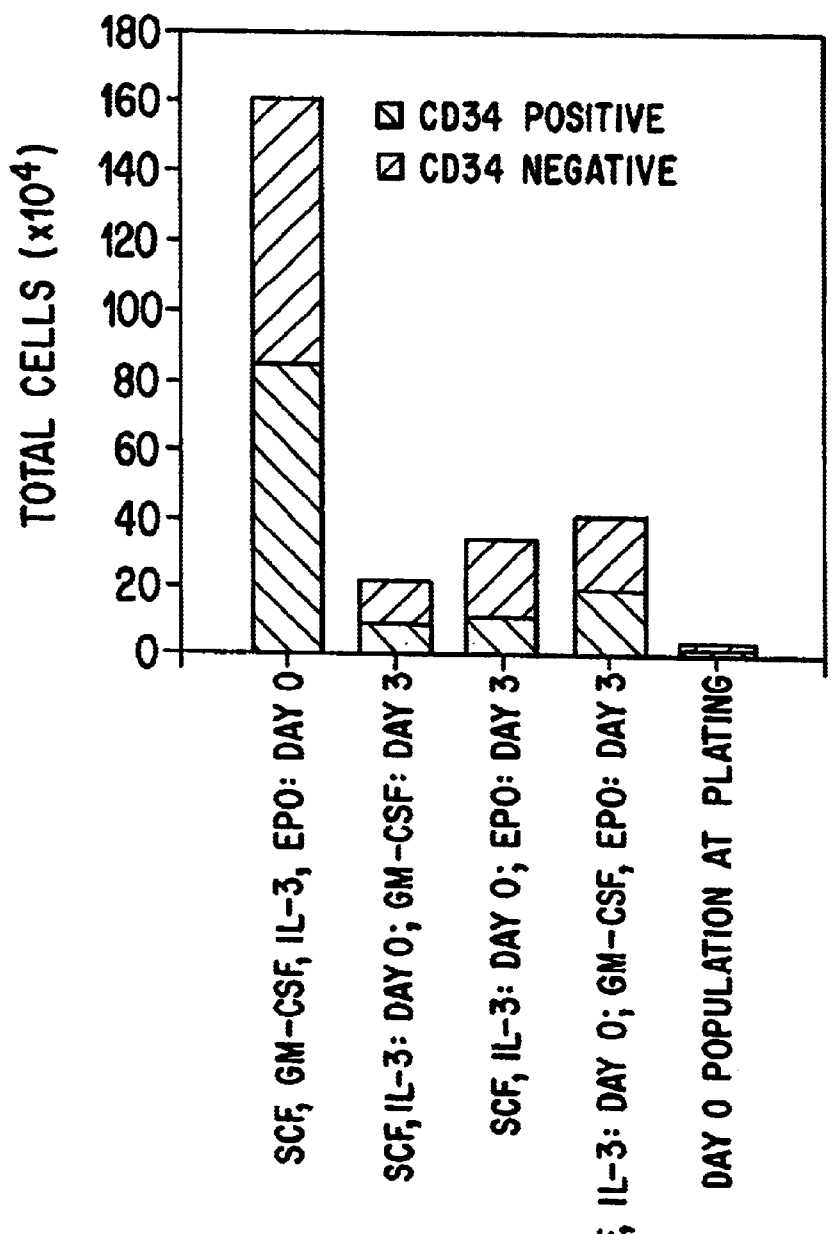
FIG. 4 shows the effect of growth factor addition on both total cell expansion and CD34+ cell expansion under serum-free and serum-supplemented culture conditions.
Figure 4B:
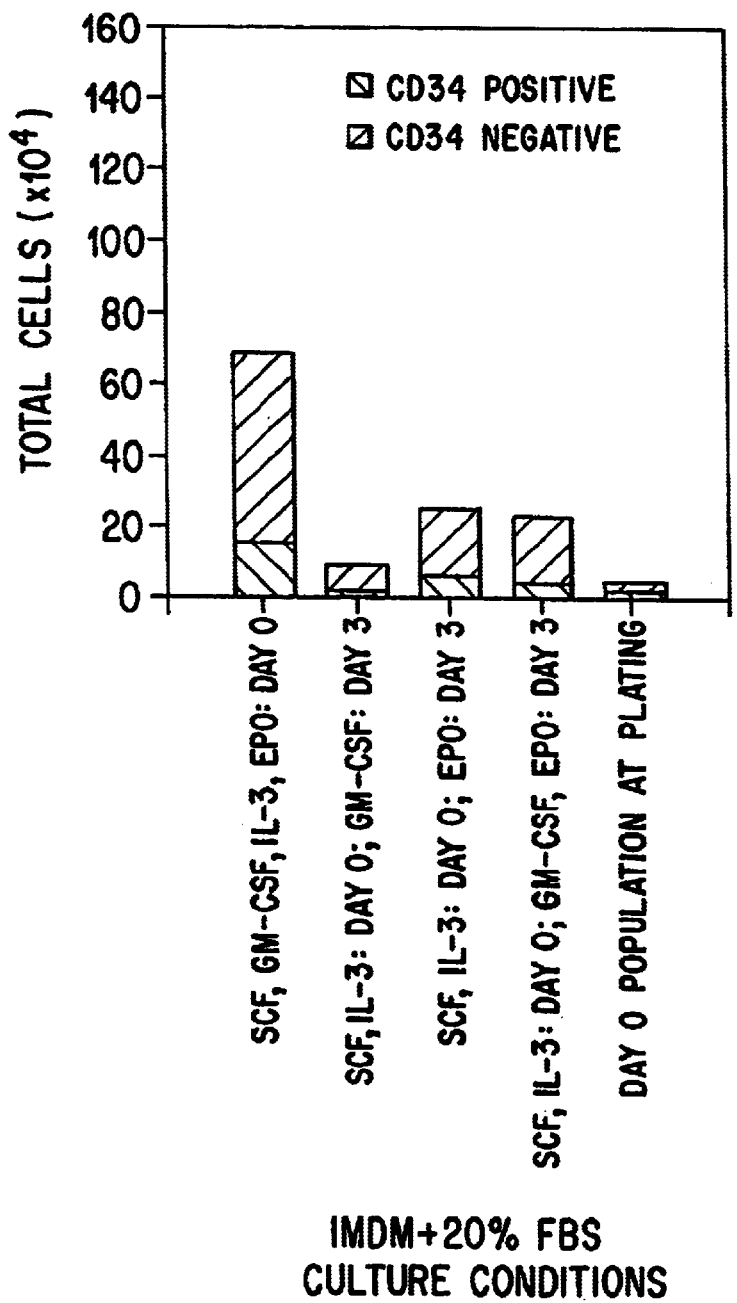

The results in FIG. 3 indicate that StemPro-34™ affords much greater control over cell expansion. Similar results are shown in FIG. 4. CD34+ selected cells from freshly harvested normal bone marrow were cultured at a seeding density of 2×10⁴ cells per mL in StemPro™-34 or IMDM +20% FBS. As indicated, human recombinant growth factors were added to final concentrations of 100 ng/mL SCF 50 ng/mL IL-3, 25 ng/mL GM-CSF, and 12 units/mL EPO at either the time of culture setup or three days after setup. After 7 days of culturing, the cells were harvested, counted, and aliquots of cells were stained for FACS analysis. In FIG. 4, CD34- cells are differentiated cells that are supported by the supplement and the medium of the invention. Such cells are red blood cell precursors (e.g., BFU-E cells) and myeloid precursors (e.g., CFU-GM and CFU-G cells).

EXAMPLE 7

Effect of Growth Factors on BFU-E Cell Development

Erythropoietin (EPO) and interleukin 6 (IL-6) stimulate the differentiation of $CD34^+$ hematopoietic cells into BFU-E cells. Differentiation of $CD34^+$ cells was evaluated using StemPro-34™ SFM. $CD34^+$ selected cells from normal bone marrow were plated at a density of $2\times10^4$ cells/mL (in triplicate) in the indicated medium using a combination of human recombinant cytokines (SCF (100 ng/mL), IL-3 (50 ng/mL), GM-CSF (25 ng/mL) IL-6 (20 ng/mL) (final concentrations)) and the concentrations of EPO shown in the inset in FIG. 5.

Figure 5:
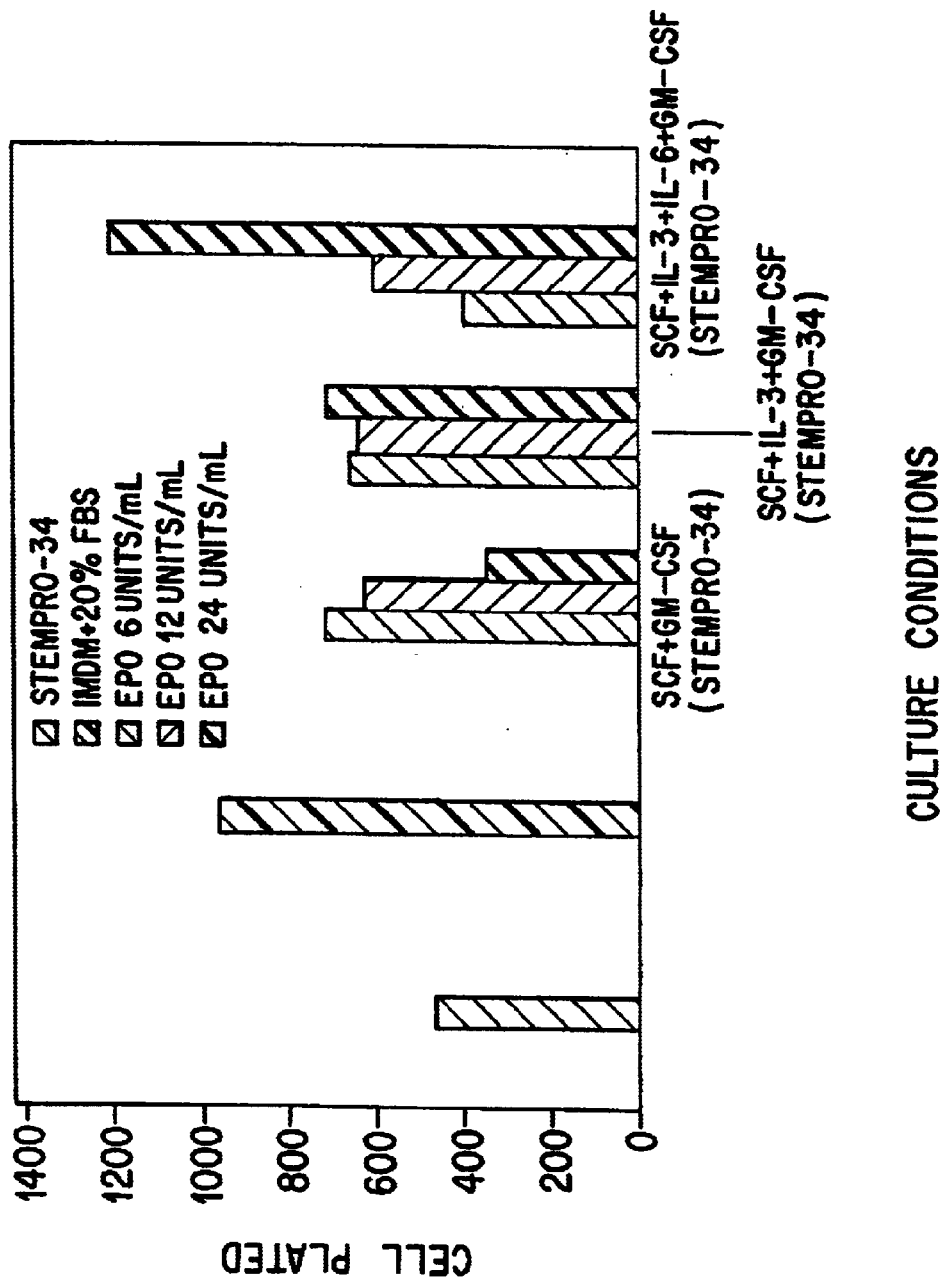
FIG. 5 shows the effect of recombinant growth factors on the development of erythroid blast-forming unit (BFU-E) cells in serum-free and serum supplemented media.

After seven days of culturing, aliquots of the expanded cell population were then plated in a methylcellulose CFU assay. Briefly, cells to be assayed for colony-forming unit function were diluted in IMDM prior to plating. Freshly selected $CD34^+$ cells were plated at a seeding density of $1\times10^3$ cells/well. After culturing for 6–8 days, cells were plated at a seeding density of $2\times10^4$ cells/well. Colonies were enumerated on day 14 of culture for BFU-E and CFU-GM colonies using standard methylcellulose systems (StemPro Complete Methylcellulose Medium, Life Technologies). Data shown in FIG. 5 are for BFU-E cells.

Serum contains undefined components which promote BFU-E colony development (Migliaccio, G. et al., *Expl. Hematol.* 18:1049 (1990)). Thus, the effects of EPO and IL-6 would be difficult, if not impossible, to interpret using serum-supplemented medium. Accordingly, it will be evident to one of ordinary skill in the art that the supplement and the medium of the present invention facilitate the controlled study of hematopoietic cell differentiation.

EXAMPLE 8

Optimization of Various Supplement Ingredients

Several ingredients of the supplement and the medium of the formulation were shown to have functional activity over a range of different concentrations. These components included transferrin, human serum albumin, HUMAN EX-CYTE®, 2-mercaptoethanol and N-acetyl-L-cysteine.

A. Transferrin

Figure 6:
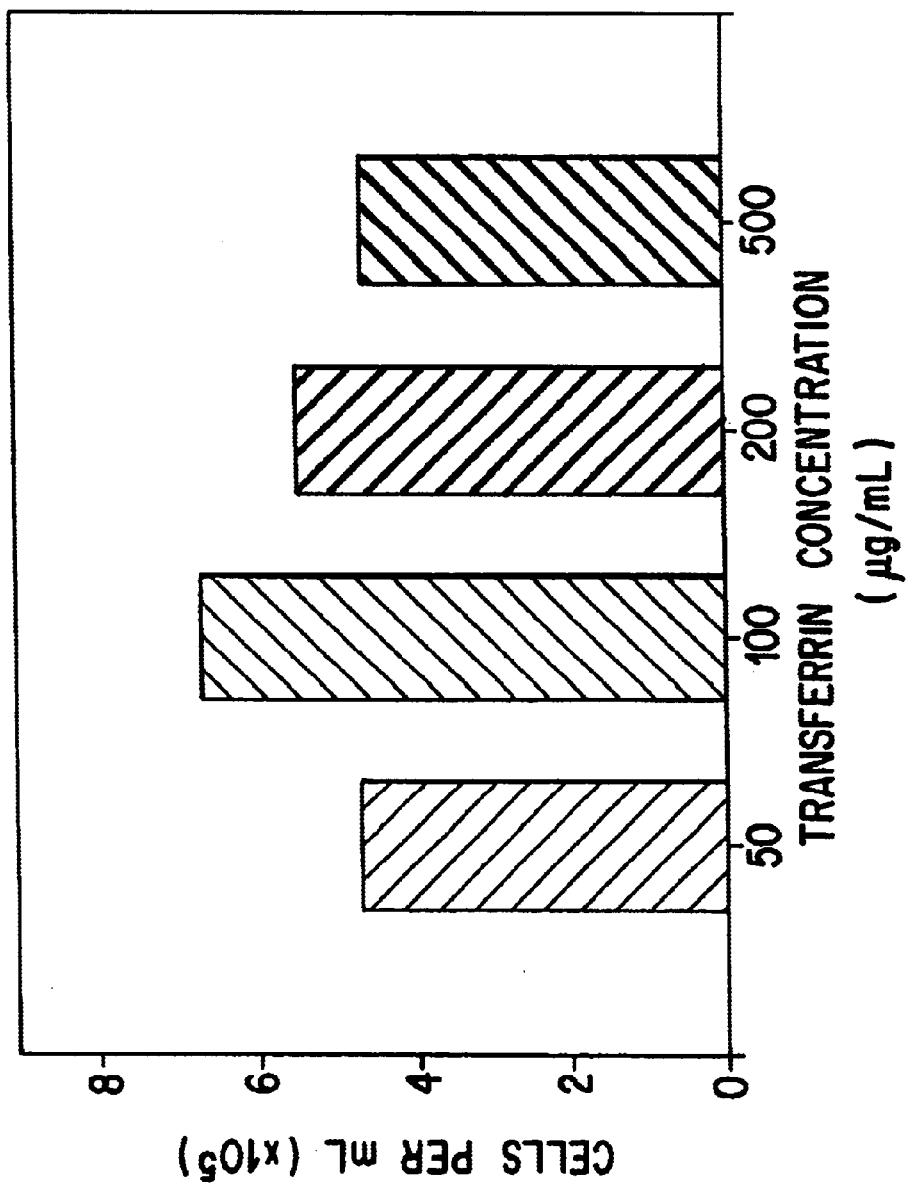
FIG. 6 shows the results of experiments in which the concentration of transferrin was optimized.

Normal human bone marrow cells were cultured in StemPro-34™ SMF medium, to which transferrin was added to the final concentrations indicated in FIG. 6. After six days in culture, cells were harvested and counted. A concentration of 100 μg/mL human transferrin proved optimal. As indicated, however, other concentrations of human transferrin support cell growth.

B. Human Ex-Cyte®

Figure 7:
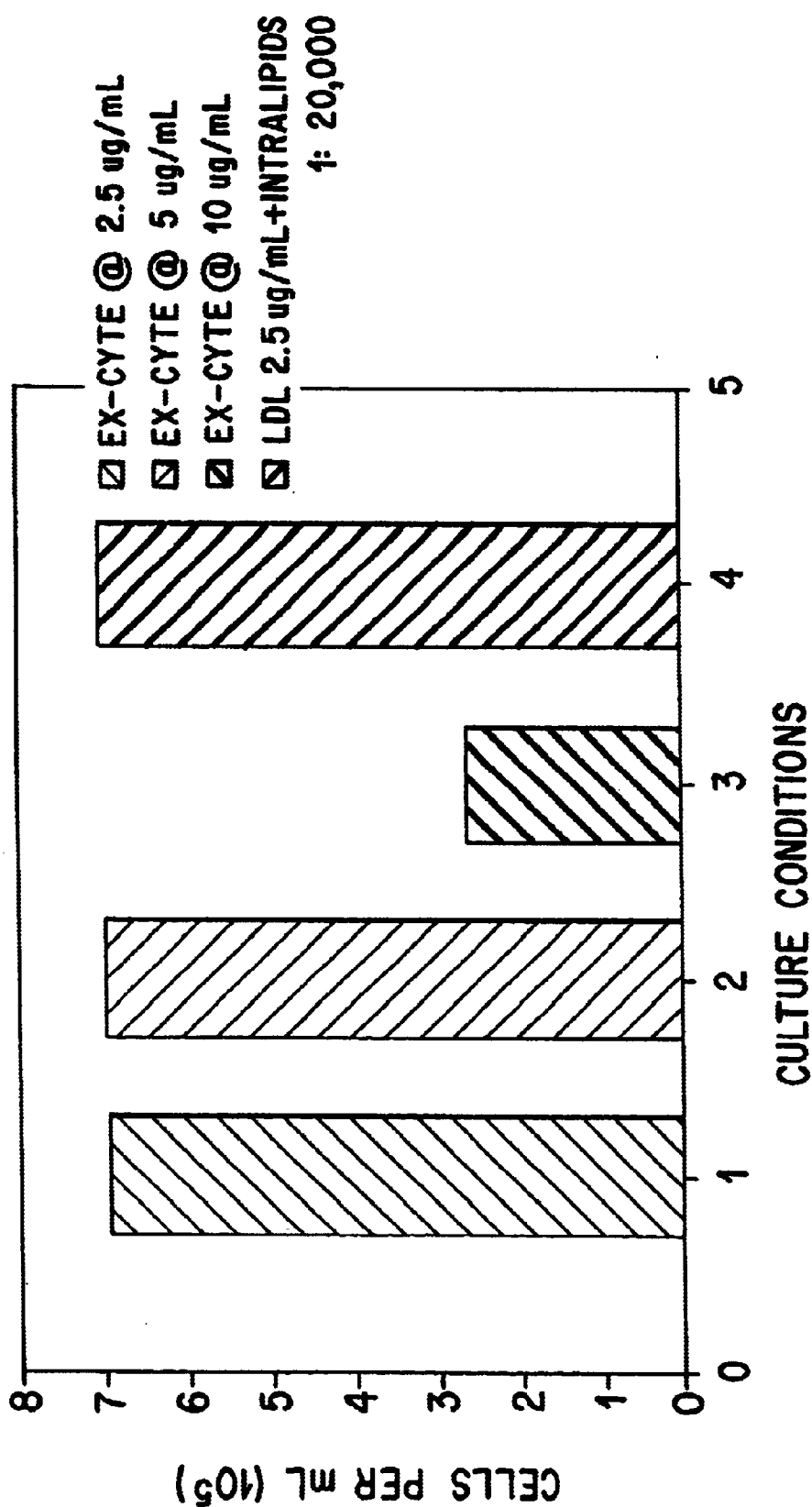
FIG. 7 shows experimental results which depict the optimization and equivalence of HUMAN EX-CYTE® to lipids and fatty acids.

$CD34^+$ cells were cultured in Stem-Pro-34™ SFM to which various lipid/fatty acid mixtures were added to the final concentrations indicated in FIG. 7. After 6–7 days in culture, cells were harvested and counted.

The combination of lipids and fatty acids, as supplied by Human Ex-Cyte®, worked optimally when HUMAN EX-CYTE® was present in the range of 5 mg/L (5 μg/mL) as shown in FIG. 7. HUMAN EX-CYTE® worked as well as a combination of LDL's and lipids, supplied as "Intralipids" by Kabi Pharmaceuticals.

Figure 8:
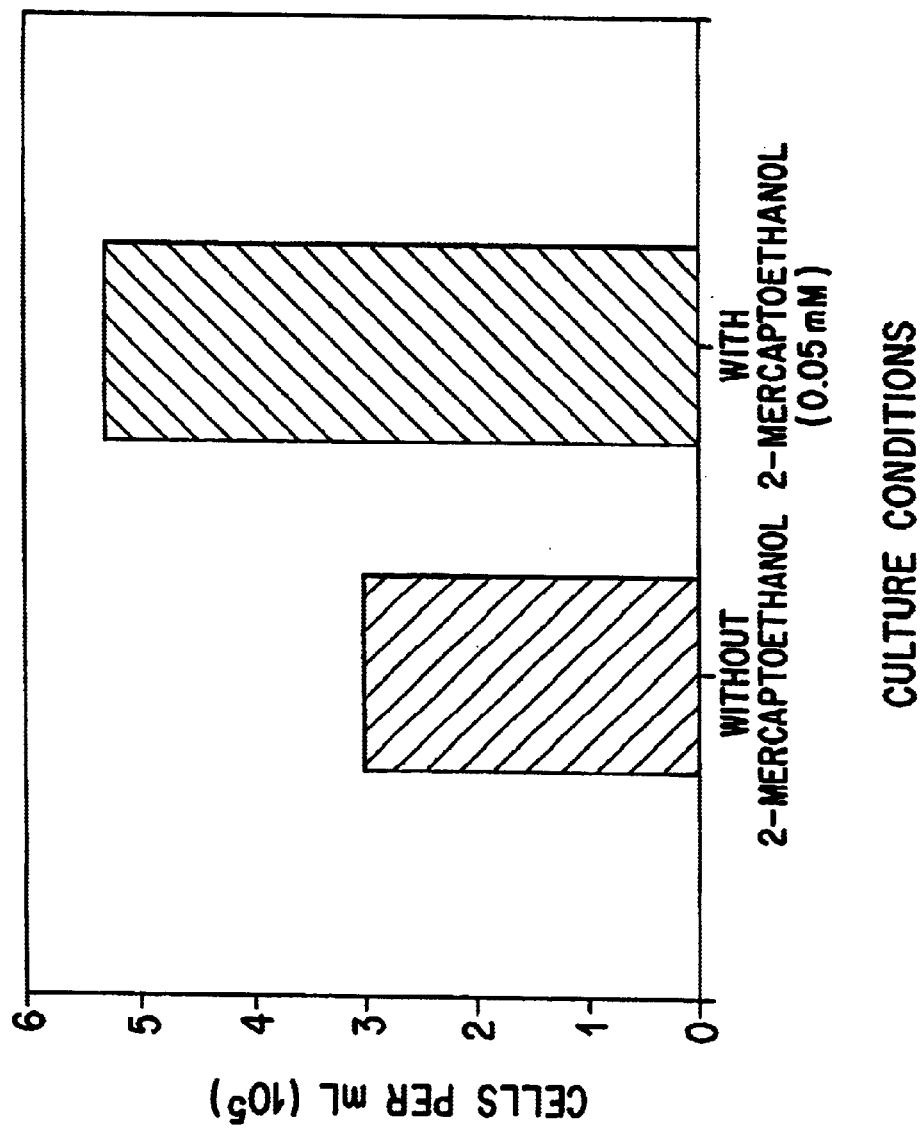
FIG. 8 shows the effect of 2-mercaptoethanol on the expansion of human bone marrow cells in serum-free culture.

C. 2-Mercaptoethanol $CD34^+$ cells were cultured in StemPro-34™ SFM, with or without 0.05 mM 2-mercaptoethanol (final concentration). After 6–7 days in culture, cells were harvested and counted. The results are shown in FIG. 8. The antioxidant 2-mercaptoethanol used at a final concentration of 4.34 mg/L enhanced performance approximately 2 fold.

Figure 9:
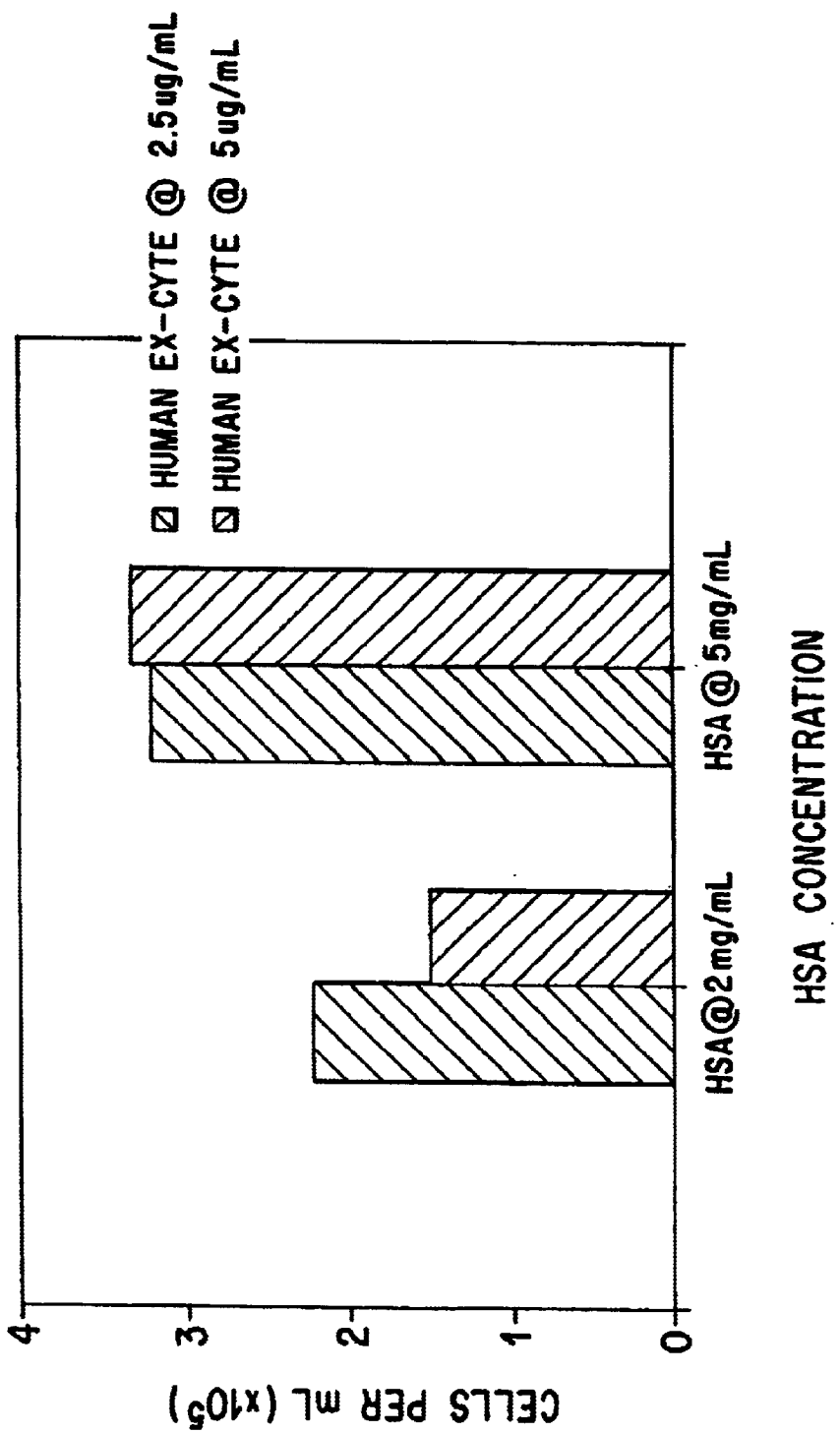
FIG. 9 shows the effect of human serum albumin concentration on expansion of CD34+ cells.

D. Human Serum Albumin Concentration $CD34^+$ cells were cultured in StemPro-34™ SFM, to which the final concentrations of human serum albumin and HUMAN EX-CYTE indicated in FIG. 9 were added. After 6–7 days in culture, cells were harvested and counted. In a preferred embodiment of the present invention, human serum albumin, is employed at a final concentration of 5 mg/L when HUMAN EX-CYTE® is used at a concentration of 5 mg/L.

EXAMPLE 9

Figure 10:
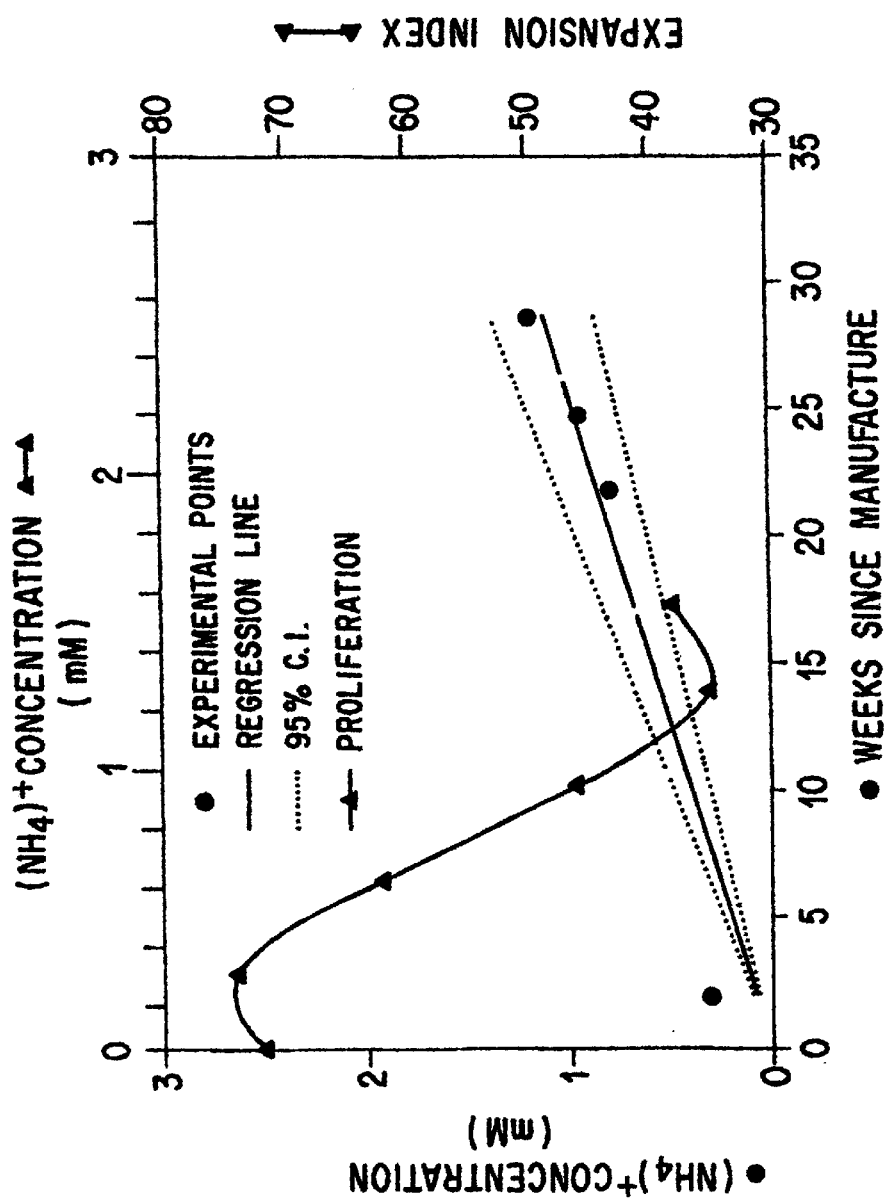
FIG. 10 shows the effect of ammonium ion concentration on the proliferation of CD34+-selected cells.

Identification of Requirement for N-acetyl-L-cysteine for Long-Term Performance Ammonia is a moiety which is toxic to hematopoietic cells. In culture, ammonia takes the form of the ammonium ion ($NH_4^+$). As shown in FIG. 10, ammonium ion breaks down spontaneously in liquid formulations. The effect of ammonium ion concentration on cell expansion was evaluated. $CD34^+$ cells were seeded at an initial density of $2\times10^4$ cells/well, in duplicate, in 24 well flat bottomed plates. Media used in these experiments were freshly made and ammonium was titrated into the medium at the indicated concentrations. All wells were then supplemented with human recombinant SCF to 100 ng/mL, IL-3 to 50 ng/mL, and GM-CSF to 25 ng/mL (final concentrations). After 6 days in culture, cells were harvested and the ammonium concentration was determined using a calibrated ammonium probe.

Figure 11:
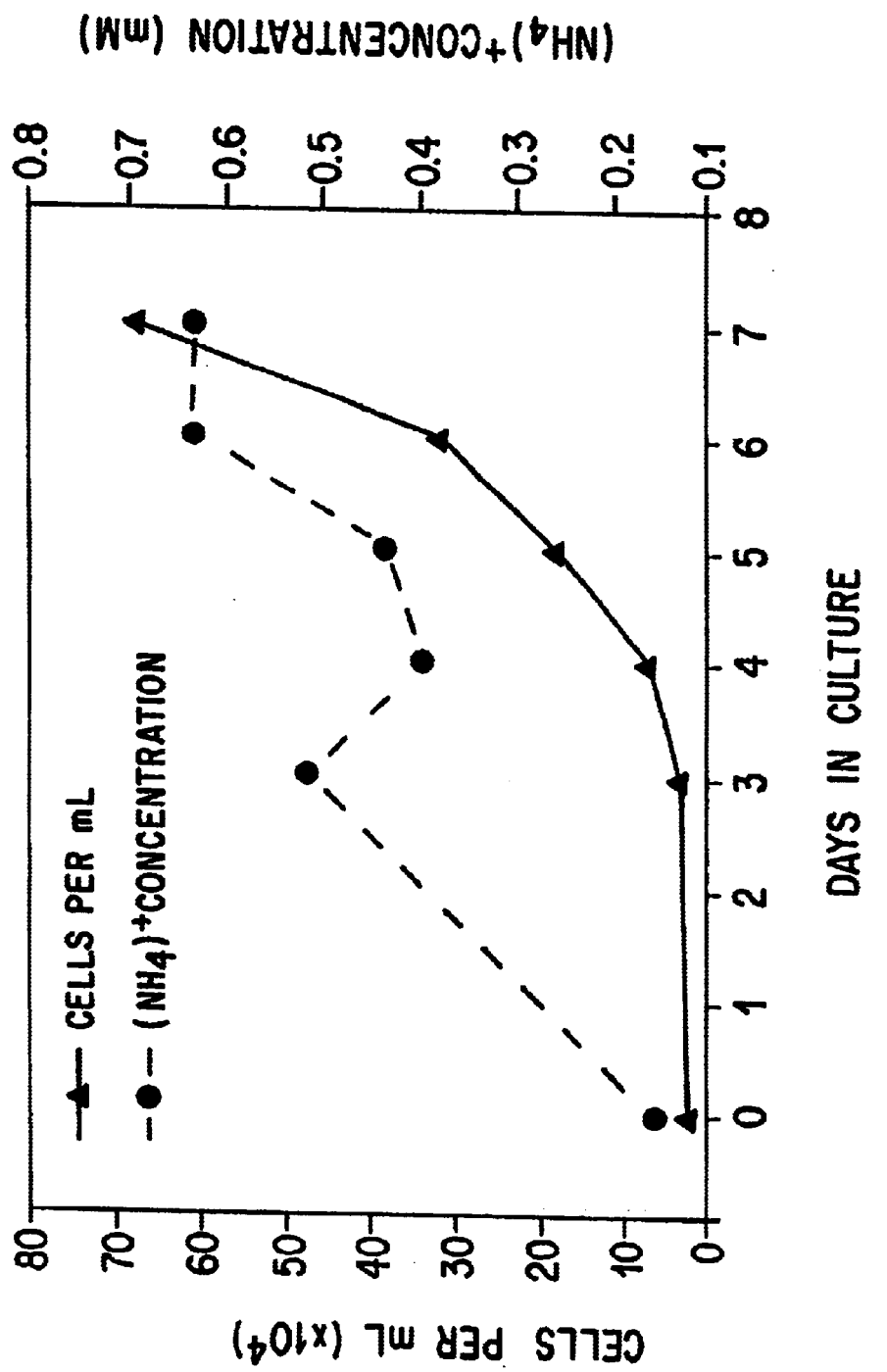
FIG. 11 shows the correlation of the generation of ammonia as a function of cell expansion.

Further, as shown in FIG. 11, the cells themselves generate even more ammonium over time. $CD34^+$ cells were seeded at an initial density of $2\times10^4$ cells/well, in duplicate, in 24 well flat bottomed plates. At the indicated time intervals, aliquots of medium were analyzed for ammonium using a calibrated ammonium probe. Aliquots of medium were also taken for cell counting by hemocytometer.

Further, oxidative species are generated by interaction of light with light-sensitive vitamins. Moreover, oxidation of reactive lipids and fatty acids leads to a time-dependent decline in the ability of serum-free media to support the growth and expansion of hematopoietic cells in culture. Thus, the shelf-life of any medium is severely limited. An advantage provided by the present invention is the long shelf-life of the supplement and the medium of the present invention. The present inventors have discovered that addition of an antioxidant (preferably, N-acetyl-L-cysteine or its derivatives) to the supplement or the medium of the present invention results in a dramatically lengthened shelf life.

Figure 12:
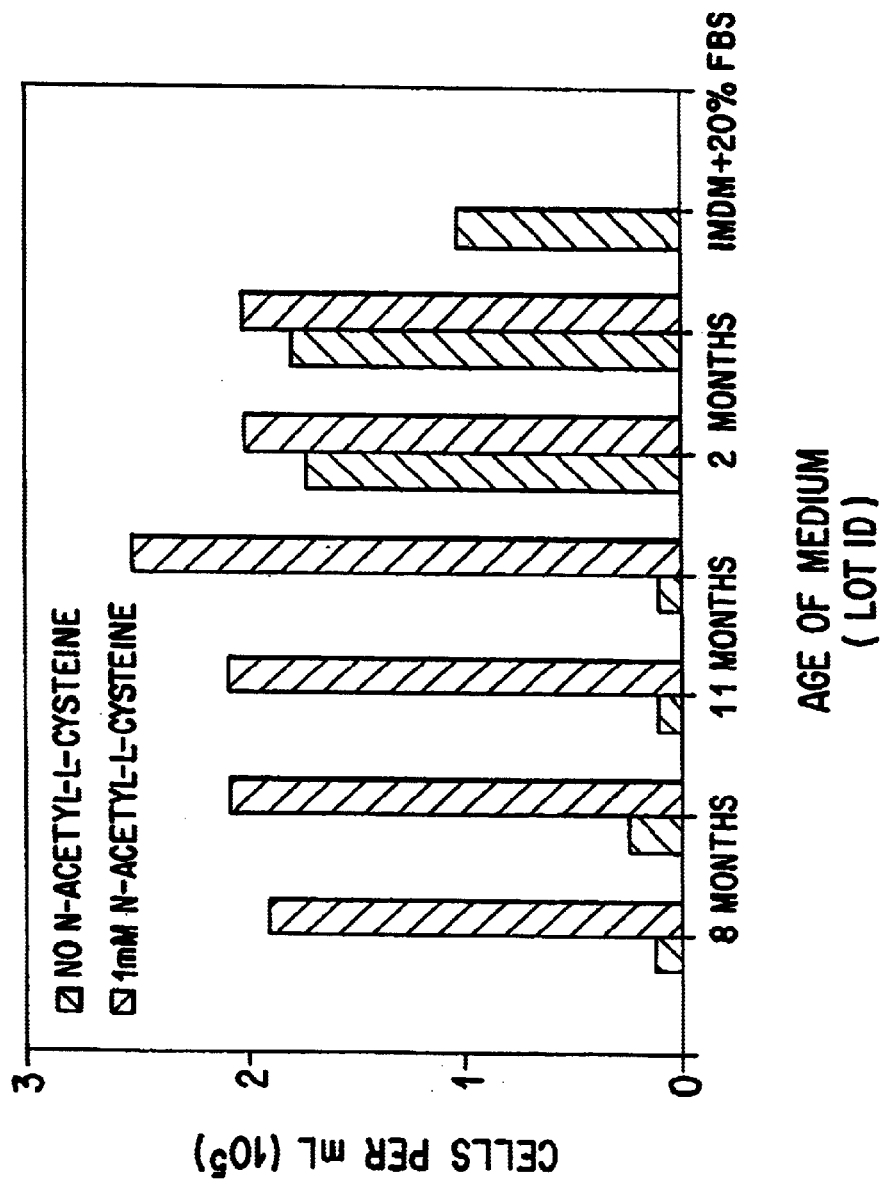
FIG. 12 reflects the requirement for N-acetyl-L-cysteine for optimal long-term performance of the serum-free medium of the present invention.

Medium formulated without N-acetyl-L-cysteine shows a marked decline in performance at about weeks 12–16 after its manufacture. As can be seen from FIG. 12, the addition of N-acetyl-L-cysteine to an "aged," inactivated medium improves the performance of the medium. $CD34^+$ selected cells from normal bone marrow were plated at a density of $2\times10^4$ cells/mL in StemPro-34™ SFM formulated with or without N-acetyl-L-cysteine at the times indicated in FIG. 12. All cultures were supplemented with the recombinant human growth factors SCF (100 ng/mL), IL-3 (50 ng/mL), and GM-CSF (25 ng/mL) (final concentrations).

Figure 13:
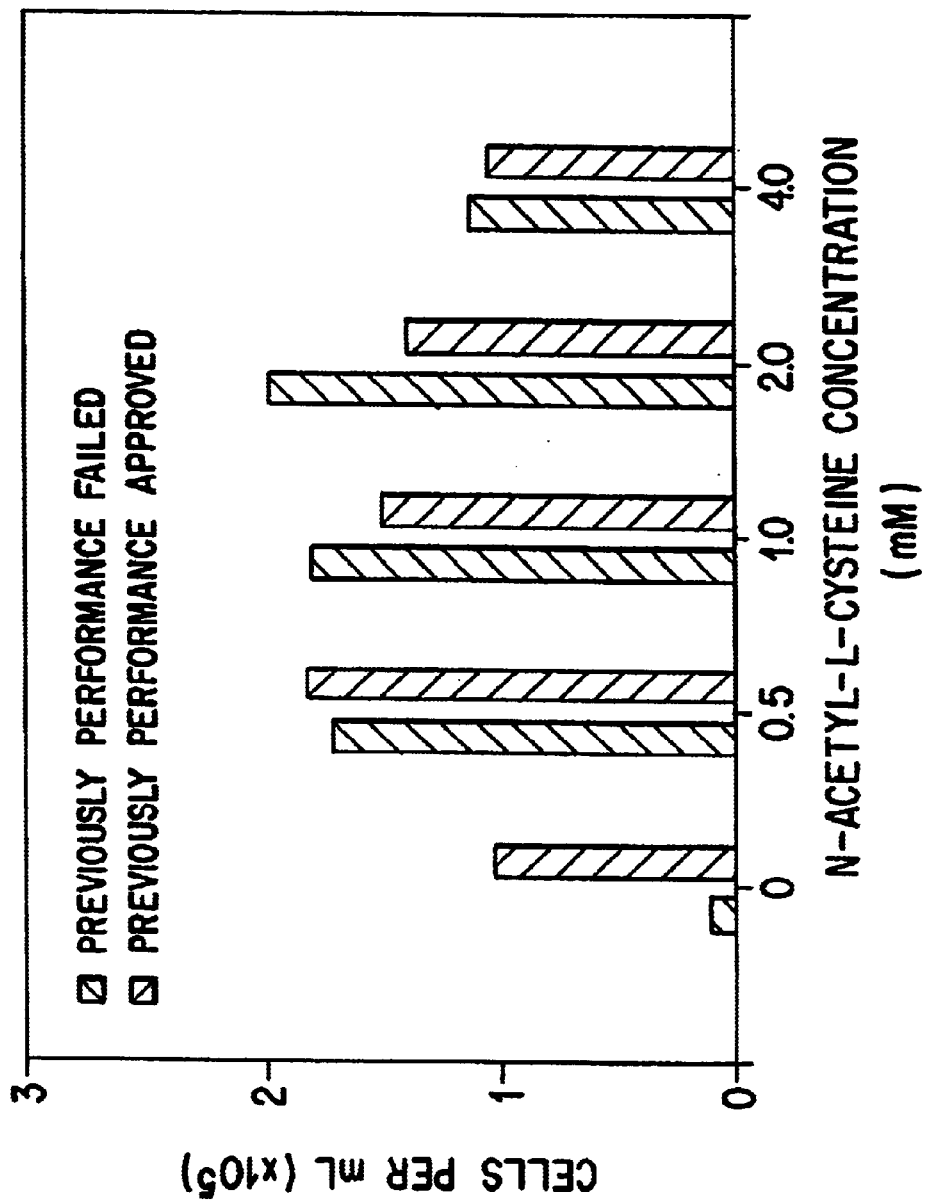
FIG. 13 shows the effect of N-acetyl-L-cysteine concentration on the performance of the serum-free supplement of the present invention.

In a preferred embodiment of the present invention, a final concentration of addition of 1.0 mM (164 mg/L) N-acetyl-L-cysteine is used. However, as the results in FIG. 13 indicate, that N-acetyl-L-cysteine increase the performance of the medium over a range of concentrations. Inclusion of N-acetyl-L-cysteine in the supplement or the medium of the present invention, at the time the supplement or the medium is formulated, increases the shelf-life of the supplement and the medium.

EXAMPLE 10

Figure 14:
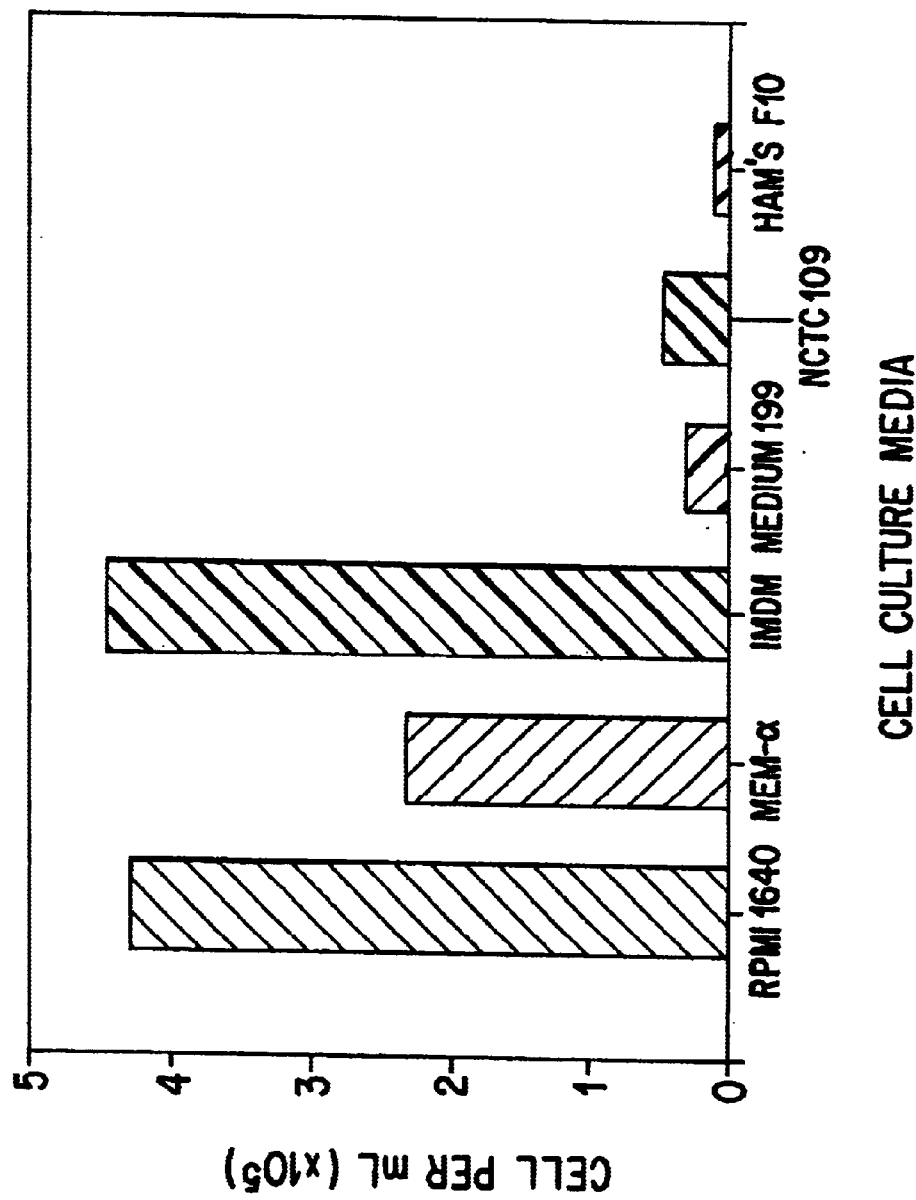
FIG. 14 shows the effect of basal medium formulation on the expansion of human bone marrow cells using the serum-free supplement of the present invention.

The supplement of the present invention can be used with any of a number of different basal media to culture hematopoietic cells. CD34$^+$ selected cells from normal bone marrow were plated at a density of $2\times10^4$ cells/mL in RPMI 1640, MEM-α, IMDM, Medium 199, NCTC 109, or Ham's F10 media. Each of these media can be purchased from Life Technologies, Inc. All cultures were supplemented with the recombinant human growth factors SCF (100 ng/mL), IL-3 (50 ng/mL), and GM-CSF (25 ng/mL) (final concentrations). As shown in FIG. 14, a number of media formulations can be used with the supplement of the present invention to support the growth and expansion of CD34$^+$ cells.

All publications, patent applications, and patents are herein incorporated by reference to the same extent as if each individual publication, patent application, or patent was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A serum-free, eukaryotic cell culture medium comprising the ingredients N-acetyl-L-cysteine, 2-mercaptoethanol, human serum albumin, D,L-tocopherol acetate, soluble human lipids for serum-free media, ethanolamine, human zinc insulin, iron-saturated transferrin, Se$^{4+}$, hydrocortisone, Ca$^{2+}$, K$^+$, Mg$^{2+}$, Na$^+$, Co$_3^{2-}$, PO$_4^{3-}$, D-glucose, HEPES, sodium pyruvate, phenol red, glycine, L-alanine, L-asparagine, L-cysteine, L-aspartic acid, L-glutamic acid, L-phenylalanine, L-histidine, L-isoleucine, L-lysine, L-leucine, L-glutamine, L-arginine HCL, L-methionine, L-proline, L-hydroxyproline, L-serine, L-threonine, L-tryptophan, L-tyrosine, L-valine, biotin, D-calcium pantothenate, choline chloride, folic acid, i-inositol, niacinamide, pyridoxal HCl, riboflavin, thiamine HCl, and vitamin B$_{12}$,
  wherein each of said ingredients is present in said medium at a concentration that supports the expansion of CD34$^+$ hematopoietic cells in suspension culture in the absence of stromal cells.

2. The serum-free, eukaryotic cell culture medium according to claim 1, wherein said medium is obtained by combining water and the ingredients of claim 1.

3. A method of making a serum-free, eukaryotic cell culture medium said method comprising admixing water and the ingredients according to claim 1.

4. A method of expanding CD34$^+$ hematopoietic cells, said method comprising (a) contacting said cells with a serum-free medium; and (b) culturing said cells in serum-free suspension culture, in the absence of stromal cells, under conditions that facilitate the expansion of said cells.

5. The method according to claim 4, said method further comprising adding a hematopoietic cell growth factor to said medium.

6. A method of expanding recombinant CD34$^+$ hematopoietic cells in serum-free culture, said method comprising (a) obtaining recombinant CD34$^+$ hematopoietic cells by introducing a nucleic acid construct into CD34$^+$ hematopoietic cells; and (b) expanding said cells in serum-free suspension culture, in the absence of stromal cells, to form a population of recombinant cells.

7. A method of providing a recombinant CD34$^+$ hematopoietic cell to a mammal, said method comprising (a) obtaining a recombinant CD34$^+$ hematopoietic cell containing a nucleic acid molecule which encodes a protein of interest;

(b) expanding said cell in serum-free suspension culture, in the absence of stromal cells, to form a population of recombinant CD34$^{30}$ hematopoietic stem cells; and (c) introducing said recombinant cells into said mammal.

8. A serum-free, eukaryotic cell culture medium supplement comprising the following ingredients at about the following concentrations:

| Ingredient | Concentration Range (mg/L) (About) |
|---|---|
| Human Serum Albumin | 1000–15,000 |
| Soluble human lipids for serum-free media | 1–15 |
| Ethanolamine | 1–25 |
| Sodium Selenite | 0.0001–0.01 |
| Hydrocortisone | 0.003–0.07 |
| D,L-Tocopherol | 0.005–0.05 |
| Iron Saturated Human Transferrin | 10–500 |
| Human Zinc Insulin | 1–25 |
| N-acetyl-L-cysteine | 16–660 |
| 2-Mercaptoethanol | 2–8. |

9. The serum-free, eukaryotic cell culture medium supplement of claim 8, wherein said ingredients are present in said medium at the following concentrations:

| Ingredient | Concentration(mg/L) (About) |
|---|---|
| Human Serum Albumin | 5000 |
| Soluble human lipids for serum-free media | 5.0 |
| Ethanolamine | 10 |
| Sodium Selenite | 0.005 |
| Hydrocortisone | 0.04 |
| D,L-Tocopherol | 0.02 |
| Iron Saturated Human Transferrin | 100 |
| Human Zinc Insulin | 10 |
| N-acetyl-L-cysteine | 160 |
| 2-Mercaptoethanol | 4. |

10. A serum-free, eukaryotic cell culture medium, wherein said medium is a 1×medium, wherein said medium contains the following ingredients at the following concentrations:

| Ingredient | Concentration Range (mg/L) (About) |
|---|---|
| CaCl₂ | 1–500 |
| KCl | 1–500 |
| KNO₃ | 0.008–0.8 |
| MgSO₄ | 10–500 |
| NaCl | 3000–9000 |
| NaHCO₃ | 100–4000 |
| NaH₂PO₄ · water | 10–750 |
| L-Alanine | 5–250 |
| L-Asparagine (free base) | 5–150 |
| L-Arginine HCl | 10–250 |
| L-Aspartic Acid | 5–125 |
| L-Cystine 2 · HCl | 1–200 |
| L-Glutamic Acid | 5–500 |
| Glycine | 5–200 |
| L-Histidine · HCl · water | 5–200 |
| L-Isoleucine | 5–500 |
| L-Leucine | 25–500 |
| L-Methionine | 5–500 |
| L-Phenylalanine | 5–500 |
| L-Proline | 5–500 |
| L-Serine | 5–500 |
| L-Threonine | 5–500 |
| L-Lysine · HCl | 25–500 |
| L-Tryptophan | 2–100 |
| L-Tyrosine (disodium salt) | 25–500 |
| L-Valine | 5–500 |
| Biotin | 0.01–1.0 |
| D-Ca Pantothentate | 0.05–10.0 |
| Choline Chloride | 1–150 |
| Folic Acid | 0.1–10.0 |
| i-Inositol | 1–75 |
| Niacinamide | 0.1–10.0 |
| Pyridoxal · HCl | 0.1–10.0 |
| Riboflavin | 0.01–2.0 |
| Thiamine · HCl | 0.1–10.0 |
| Vitamin B₁₂ | 0.001–5.0 |
| Human Serum Albumin | 1000–15,000 |
| Na₂SeO₃ | 0.001–0.01 |
| D-Glucose | 2000–9000 |
| Phenol Red | 0.5–30 |
| HEPES | 1000–7000 |
| Sodium Pyruvate | 10–300 |
| Soluble human lipids for serum-free media | 1–15 |
| Ethanolamine | 1–25 |
| Hydrocortisone | 0.003–0.07 |
| D,L-Tocopherol | 0.005–0.05 |
| Iron Saturated Human Transferrin | 10–500 |
| Human Zinc Insulin | 1–25 |
| N-acetyl-L-cysteine | 16–660 |
| 2-Mercaptoethanol | 2–8, | and wherein said medium supports the expansion of CD34⁺ cells in serum-free culture.

11. The serum-free, eukaryotic cell culture medium of claim 10, wherein said medium supports the expansion of CD34⁺ cells in suspension culture.

12. The serum-free, eukaryotic cell culture medium of claim 10, wherein said medium supports the expansion of CD34⁺ hematopoietic cells in the absence of stromal cells.

13. The serum-free, eukaryotic cell culture medium according to claim 10, wherein said ingredients in said 1×medium are present at the following concentrations:

| Ingredient | Concentration (mg/L) (About) |
|---|---|
| CaCl₂ | 165 |
| KCl | 330 |
| KNO₃ | 0.08 |
| MgSO₄ | 100 |
| NaCl | 4,500 |
| NaHCO₃ | 3,000 |
| NaH₂PO₄ · water | 125 |
| L-Alanine | 25 |
| L-Asparagine (free base) | 25 |
| L-Arginine HCl | 84 |
| L-Aspartic Acid | 30 |
| L-Cystine 2 · HCl | 90 |
| L-Glutamic Acid | 75 |
| Glycine | 30 |
| L-Histidine · HCl · water | 42 |
| L-Isoleucine | 105 |
| L-Leucine | 105 |
| L-Methionine | 30 |
| L-Phenylalanine | 70 |
| L-Proline | 40 |
| L-Serine | 40 |
| L-Threonine | 100 |
| L-Lysine · HCl | 150 |
| L-Tryptophan | 15 |
| L-Tyrosine (disodium salt) | 100 |
| L-Valine | 95 |
| Biotin | 0.01 |
| D-Ca Pantothentate | 4 |
| Choline Chloride | 4 |
| Folic Acid | 4.00 |
| i-Inositol | 7 |
| Niacinamide | 4 |
| Pyridoxal · HCl | 4 |
| Riboflavin | 0.04 |
| Thiamine · HCl | 4 |
| Vitamin B₁₂ | 0.001 |
| Human Serum Albumin | 5000 |
| Na₂SeO₃ | 0.02 |
| D-Glucose | 4500 |
| Phenol Red | 15 |
| HEPES | 6000 |
| Sodium Pyruvate | 110 |
| Soluble human lipids for serum-free media | 5 |
| Ethanolamine | 10 |
| Hydrocortisone | 0.04 |
| D,L-Tocopherol | 0.02 |
| Iron Saturated Human Transferrin | 100 |
| Human Zinc Insulin | 10 |
| N-acetyl-L-cysteine | 160 |
| 2-Mercaptoethanol | 4. |

14. A method of making a serum-free, eukaryotic cell culture medium, comprising admixing water and the following ingredients at the following concentrations to form a 1×medium:

| Ingredient | Concentration Range (mg/L) (About) |
|---|---|
| CaCl₂ | 1–500 |
| KCl | 1–500 |
| KNO₃ | 0.008–0.8 |
| MgSO₄ | 10–500 |
| NaCl | 3000–9000 |
| NaHCO₃ | 100–4000 |
| NaH₂PO₄ · water | 10–750 |
| L-Alanine | 5–250 |

-continued

| Ingredient | Concentration Range (mg/L) (About) |
|---|---|
| L-Asparagine (free base) | 5–150 |
| L-Arginine HCl | 10–250 |
| L-Aspartic Acid | 5–125 |
| L-Cystine 2 · HCl | 1–200 |
| L-Glutamic Acid | 5–500 |
| Glycine | 5–200 |
| L-Histidine · HCl · water | 5–200 |
| L-Isoleucine | 5–500 |
| L-Leucine | 25–500 |
| L-Methionine | 5–500 |
| L-Phenylalanine | 5–500 |
| L-Proline | 5–500 |
| L-Serine | 5–500 |
| L-Threonine | 5–500 |
| L-Lysine · HCl | 25–500 |
| L-Tryptophan | 2–100 |
| L-Tyrosine (disodium salt) | 25–500 |
| L-Valine | 5–500 |
| Biotin | 0.01–1.0 |
| D-Ca Pantothentate | 0.05–10.0 |
| Choline Chloride | 1–150 |
| Folic Acid | 0.1–10.0 |
| i-Inositol | 1–75 |
| Niacinamide | 0.1–10.0 |
| Pyridoxal · HCl | 0.1–10.0 |
| Riboflavin | 0.01–2.0 |
| Thiamine · HCl | 0.1–10.0 |
| Vitamin $B_{12}$ | 0.001–5.0 |
| Human Serum Albumin | 1000–15,000 |
| $Na_2SeO_3$ | 0.001–0.01 |
| D-Glucose | 2000–9000 |
| Phenol Red | 0.5–30 |
| HEPES | 1000–7000 |
| Sodium Pyruvate | 10–300 |
| Soluble human lipids for serum-free media | 1–15 |
| Ethanolamine | 1–25 |
| Hydrocortisone | 0.003–0.07 |
| D,L-Tocopherol | 0.005–0.05 |
| Iron Saturated Human Transferrin | 10–500 |
| Human Zinc Insulin | 1–25 |
| N-acetyl-L-cysteine | 16–660 |
| 2-Mercaptoethanol | 2–8, | wherein said medium supports the expansion of CD34$^+$ hematopoietic cells in serum-free culture.

15. The method according to claim 14, wherein said ingredients are admixed with water at the following concentrations:

| Ingredient | Concentration (mg/L) (About) |
|---|---|
| $CaCl_2$ | 165 |
| KCl | 330 |
| $KNO_3$ | 0.08 |
| $MgSO_4$ | 100 |
| NaCl | 4,500 |
| $NaHCO_3$ | 3,000 |
| $NaH_2PO_4$ · water | 125 |
| L-Alanine | 25 |
| L-Asparagine (free base) | 25 |
| L-Arginine HCl | 84 |
| L-Aspartic Acid | 30 |
| L-Cystine 2 · HCl | 90 |
| L-Glutamic Acid | 75 |
| Glycine | 30 |
| L-Histidine · HCl · water | 42 |

-continued

| Ingredient | Concentration (mg/L) (About) |
|---|---|
| L-Isoleucine | 105 |
| L-Leucine | 105 |
| L-Methionine | 30 |
| L-Phenylalanine | 70 |
| L-Proline | 40 |
| L-Serine | 40 |
| L-Threonine | 100 |
| L-Lysine · HCl | 150 |
| L-Tryptophan | 15 |
| L-Tyrosine (disodium salt) | 100 |
| L-Valine | 95 |
| Biotin | 0.01 |
| D-Ca Pantothentate | 4 |
| Choline Chloride | 4 |
| Folic Acid | 4.00 |
| i-Inositol | 7 |
| Niacinamide | 4 |
| Pyridoxal · HCl | 4 |
| Riboflavin | 0.04 |
| Thiamine · HCl | 4 |
| Vitamin $B_{12}$ | 0.001 |
| Human Serum Albumin | 5000 |
| $Na_2SeO_3$ | 0.02 |
| D-Glucose | 4500 |
| Phenol Red | 15 |
| HEPES | 6000 |
| Sodium Pyruvate | 110 |
| Soluble human lipids for serum-free media | 5 |
| Ethanolamine | 10 |
| Hydrocortisone | 0.04 |
| D,L-Tocopherol | 0.02 |
| Iron Saturated Human Transferrin | 100 |
| Human Zinc Insulin | 10 |
| N-acetyl-L-cysteine | 160 |
| 2-Mercaptoethanol | 4. |

16. The medium obtained by the method of claim 14.

17. The medium obtained by the method of claim 15.

18. The medium of claim 16, wherein said medium supports the expansion of CD34$^+$ cells in suspension culture.

19. The medium of claim 16, wherein said medium supports the expansion of CD34$^+$ hematopoietic cells in the absence of stromal cells.

20. The medium obtained by the method of claim 3.

21. The method of claim 14, wherein said medium supports the expansion of CD34$^+$ hematopoietic cells in suspension culture.

22. The method of claim 21, wherein said medium supports the expansion of CD34$^+$ hematopoietic cells in the absence of stromal cells.

23. The method of claim 15, wherein said medium supports the expansion of CD34$^+$ hematopoietic cells in suspension culture.

24. The method of claim 23, wherein said medium supports the expansion of CD34$^+$ hematopoietic cells in the absence of stromal cells.

25. The medium of claim 17, wherein said medium supports the expansion of CD34$^+$ hematopoietic cells in suspension culture.

26. The medium of claim 25, wherein said medium supports the expansion of CD34$^+$ hematopoietic cells in the absence of stromal cells.

27. A method of expanding CD34$^+$ hematopoietic cells, said method comprising
    (a) contacting said cells with the serum-free medium of claim 1, and (b) culturing said cells in serum-free suspension culture, in the absence of stromal cells, under conditions that facilitate the expansion of said cells.

28. A method of expanding CD34$^+$ hematopoietic cells, said method comprising
    (a) contacting said cells with the serum-free medium of claim 20, and
    (b) culturing said cells in serum-free suspension culture, in the absence of stromal cells, under conditions that facilitate the expansion of said cells.

29. A method of expanding CD34$^+$ hematopoietic cells, said method comprising
    (a) contacting said cells with the serum-free medium of claim 10, and
    (b) culturing said cells in serum-free suspension culture, in the absence of stromal cells, under conditions that facilitate the expansion of said cells.

30. A method of expanding CD34$^+$ hematopoietic cells, said method comprising
    (a) contacting said cells with the serum-free medium of claim 13, and
    (b) culturing said cells in serum-free suspension culture, in the absence of stromal cells, under conditions that facilitate the expansion of said cells.

31. A method of expanding CD34$^+$ hematopoietic cells, said method comprising
    (a) contacting said cells with the serum-free medium of claim 16, and
    (b) culturing said cells in serum-free suspension culture, in the absence of stromal cells, under conditions that facilitate the expansion of said cells.

32. A method of expanding CD34$^+$ hematopoietic cells, said method comprising
    (a) contacting said cells with the serum-free medium of claim 17, and
    (b) culturing said cells in serum-free suspension culture, in the absence of stromal cells, under conditions that facilitate the expansion of said cells.

33. A method of expanding recombinant CD34$^+$ hematopoietic cells in serum-free culture, said method comprising expanding said recombinant cells according to the method of claim 27.

34. A method of expanding recombinant CD34$^+$ hematopoietic cells in serum-free culture, said method comprising expanding said recombinant cells according to the method of claim 28.

35. A method of expanding recombinant CD34$^+$ hematopoietic cells in serum-free culture, said method comprising expanding said recombinant cells according to the method of claim 29.

36. A method of expanding recombinant CD34$^+$ hematopoietic cells in serum-free culture, said method comprising expanding said recombinant cells according to the method of claim 30.

37. A method of expanding recombinant CD34$^+$ hematopoietic cells in serum-free culture, said method comprising expanding said recombinant cells according to the method of claim 31.

38. A method of expanding recombinant CD34$^+$ hematopoietic cells in serum-free culture, said method comprising expanding said recombinant cells according to the method of claim 32.

39. A method of providing recombinant CD34$^+$ hematopoietic cells to a mammal, said method comprising
    (a) expanding said recombinant CD34$^+$ hematopoietic cells according to the method of claim 27; and
    (b) introducing said recombinant cells into said mammal.

40. A method of providing recombinant CD34$^+$ hematopoietic cells to a mammal, said method comprising
    (a) expanding said recombinant CD34$^+$ hematopoietic cells according to the method of claim 28; and
    (b) introducing said recombinant cells into said mammal.

41. A method of providing recombinant CD34$^+$ hematopoietic cells to a mammal, said method comprising
    (a) expanding said recombinant CD34$^+$ hematopoietic cells according to the method of claim 29; and
    (b) introducing said recombinant cells into said mammal.

42. A method of providing recombinant CD34$^+$ hematopoietic cells to a mammal, said method comprising
    (a) expanding said recombinant CD34$^+$ hematopoietic cells according to the method of claim 30; and
    (b) introducing said recombinant cells into said mammal.

43. A method of providing recombinant CD34$^+$ hematopoietic cells to a mammal, said method comprising
    (a) expanding said recombinant CD34$^+$ hematopoietic cells according to the method of claim 31; and
    (b) introducing said recombinant cells into said mammal.

44. A method of providing recombinant CD34$^+$ hematopoietic cells to a mammal, said method comprising
    (a) expanding said recombinant CD34$^+$ hematopoietic cells according to the method of claim 32; and
    (b) introducing said recombinant cells into said mammal.

45. The method of claim 4, wherein said CD34$^+$ hematopoietic cells are isolated, and wherein said contacting comprises contacting said isolated CD34$^+$ hematopoietic cells with a serum-free medium.

46. A method of expanding CD34$^+$ hematopoietic cells, said method comprising:
    (a) contacting said cells with a serum-free medium comprising at least one anti-oxidant, at least one albumin or albumin substitute, at least one lipid agent, at least one insulin or insulin substitute and at least one transferrin or transferrin substitute; and
    (b) culturing said cells in serum-free suspension culture in the absence of stromal cells under conditions that facilitate said expansion of said cells.

47. The method of claim 46, wherein said serum-free medium further comprises one or more component selected from the group consisting of trace elements, glucocorticoids, inorganic salts, energy sources, buffering agents, pyruvate salts, pH indicators, amino acids, vitamins, cytokines and growth factors.

48. The method of claim 47, wherein said one or more selected components comprises at least one cytokine or growth factor.

49. The method of claim 47, wherein said one or more selected components comprises at least one amino acid.

50. The method of claim 47, wherein said one or more selected components comprises at least one trace element.

51. The method of claim 50, wherein said trace element is selenium.

52. The method of claim 47, wherein said one or more selected components comprises at least one vitamin.

53. The method of claim 52, wherein said at least one vitamin comprises vitamin B$_{12}$.

54. The method of claim 47, wherein said one or more selected components comprises at least one glucocorticoid.

55. The method of claim 54, wherein said at least one glucocorticoid comprises hydrocortisone.

56. The method of claim 46, wherein said at least one anti-oxidant comprises one or more antioxidant selected from the group consisting of N-acetyl-L-cysteine, 2-mercaptoethanol, D,L-tocopherol, and derivatives thereof.

57. The method of claim 56, wherein said at least one anti-oxidant comprises N-acetyl-L-cysteine or derivatives thereof.

58. The method of claim 46, wherein said hematopoietic cells are recombinant cells.

* * * * *